(12) United States Patent
Rio Frio et al.

(10) Patent No.: US 10,400,284 B2
(45) Date of Patent: Sep. 3, 2019

(54) METHOD FOR PREDICTING RESPONSIVENESS TO A TREATMENT WITH AN EGFR INHIBITOR

(71) Applicants: Integragen, Evry (FR); Institut National de la Sante et de la Recherche Medicale (INSERM), Paris (FR); Centre National de la Recherche Scientifique (CNRS), Paris (FR); Assistance Publique—Hopitaux de Paris, Paris (FR); Universite Paris Descartes, Paris (FR)

(72) Inventors: Thomas Rio Frio, Paris (FR); Pierre Laurent-Puig, Meudon (FR); Sandrine Imbeaud, Vitry sur Seine (FR)

(73) Assignees: INTEGRAGEN, Evry (FR); INSTITUT NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR); ASSISTANCE PUBLIQUE—HOPITAUX DE PARIS, Paris (FR); UNIVERSITE PARIS DESCARTES, Paris (FR)

( * ) Notice: Subject to any disclaimer, the term of this patent is extended or adjusted under 35 U.S.C. 154(b) by 1345 days.

(21) Appl. No.: 14/360,311

(22) PCT Filed: Nov. 23, 2012

(86) PCT No.: PCT/EP2012/073535
§ 371 (c)(1),
(2) Date: May 23, 2014

(87) PCT Pub. No.: WO2013/076282
PCT Pub. Date: May 30, 2013

(65) Prior Publication Data
US 2014/0370029 A1   Dec. 18, 2014

(30) Foreign Application Priority Data

Nov. 25, 2011 (EP) .................................. 11306568
Aug. 31, 2012 (EP) .................................. 12306042

(51) Int. Cl.
*G01N 33/48* (2006.01)
*C12Q 1/6886* (2018.01)

(52) U.S. Cl.
CPC ..... *C12Q 1/6886* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS 7,101,663 B2   9/2006   Godfrey et al.

FOREIGN PATENT DOCUMENTS

| WO | WO 2009/080437 | | 7/2009 | |
| WO | WO 2010/015538 | * | 2/2010 | ............... C12Q 1/68 |

(Continued)

OTHER PUBLICATIONS

Mosakhani et al. (Genes, Chromosomes & Cancer; 2012, 51, 1-9).*

(Continued)

*Primary Examiner* — Larry D Riggs, II
(74) *Attorney, Agent, or Firm* — Buchanan Ingersoll & Rooney PC

(57) ABSTRACT

The present invention relates to a method for predicting whether a patient with a cancer is likely to respond to an epidermal growth factor receptor (EGFR) inhibitor, which method comprises determining the expression level hsa-miR-31-3p miRNA in a sample of said patient. The inven- (Continued)

tion also relates to therapeutic uses of an EGFR inhibitor in a patient predicted to respond to said EGFR inhibitor.

17 Claims, 7 Drawing Sheets

Specification includes a Sequence Listing.

(56) References Cited

FOREIGN PATENT DOCUMENTS

| WO | WO 2010/121238 | | 10/2010 | |
|---|---|---|---|---|
| WO | WO 2011/135459 | * | 11/2011 | ............... C12Q 1/68 |

OTHER PUBLICATIONS

Albitar et al., *EGFR isoforms and gene regulation in human endometrial cancer cells*, 9(166) Molecular Cancer 1-13 (2010).
Allen et al., *Resistance May Not Be Futile: microRNA Biomarkers for Chemoresistance and Potential Therapeutics*, 9(12) Molecular Cancer Therapy 3126-3136 (Dec. 2010).
Ambros et al., *A uniform system for microRNA annotation*, 9(3) RNA 277-279 (2003).
Bair et al., *Semi-Supervised Methods to Predict Patient Survival from Gene Expression Data*, 2(4) PLoS Biology 0511-0522 (Apr. 2004).
Bos, *ras Oncogenes in Human Cancer: A Review*, 49 Cancer Research 4682-4689 (1989).
Bustin et al., *Real-time reverse transcription PCR (qRT-PCR) and its potential use in clinical diagnosis*, 109 Clinical Science 365-379 (2005).
Chan et al., *Novel systemic therapeutic for nasopharyngeal carcinoma*, 16(Suppl. 1) Expert Opin. Ther. S63-S68 (2012).
Chang et al., *Passenger strand miRNA miR-31\* regulates the phenotypes of oral cancer cells by targeting RhoA*, 49(1) Oral Oncology 27-33 (Jan. 2013) (In Press 2012).
Chu et al., *EGFR 3'UTR 774T>C polymorphism contributes to bladder cancer risk*, Mutagenesis 1-7 (2012).
Ciardiello et al., *EGFR Antagonists in Cancer Treatment*, 358(11) New England Journal of Medicine 1160-1174 (Mar. 13, 2008).
Edkins et al., *Recurrent KRAS Codon 146 Mutations in Human Colorectal Cancer*, 5(8) Cancer Biol Ther. 928-932 (Aug. 2006).
Griffiths-Jones et al., *miRBase: microRNA sequences, targets and gene nomenclature*, 34 Nucleic Acids Research D140-D144 (2006).
Griffiths-Jones et al., *MiRBase: tools for microRNA genomics*, 36 Nucleic Acids Research D154-D158 (2008).
Griffiths-Jones, *the microRNA registry*, 32 Nucleic Acids Research D109-D111 (2004).
Hatakeyama et al., *Regulation of Heparin-Binding EGF-Like Growth Factor by miR-212 and Acquired Cetuximab-Resistance in Head and Neck Squamous Cell Carcinoma*, 5(9) PLoS One 1-13 (Sep. 2010).
Kozomara et al., *miRBase: integrating microRNA annotation and deep-sequence data*, 39 Nucleic Acids Research D152-D157 (2011).
Laurent-Puig et al., *Analysis of PTEN, BRAF, and EGFR Status in Determining Benefit From Cetuximab Therapy in Wild-Type KRAS Metastatic Colon Cancer*, 27(35) Journal of Clinical Oncology 5924-5930 (Dec. 10, 2009).
Leboulleux et al., *Vandetanib in locally advanced or metastatic differentiated thyroid cancer: a randomised, double-blind, phase 2 trial*, 13 Lancet Oncology 897-905 (Sep. 2012).
Leslie et al., *Lapatinib and potential prognostic value of EGFR mutations in a Gynecologic Oncology Group phase II trial of persistent or recurrent endometrial cancer*, 127 Gynecologic ONcology 345-350 (2012).
Li et al., *VEGFR and EGFR inhibition increases epithelial cellular characteristics and chemotherapy sensitivity in mesenchymal bladder cancer cells*, 24 Oncology Reports 1019-1028 (2010).

Liebner et al., *Thyroid cancer: pathogenesis and targeted therapy*, 2 Therapeutic Advances in Endocrinology and Metabolism 173-195 (2011).
Lièvre et al., *KRAS Mutation Status Is Predictive of Response to Cetuximab Therapy in Colorectal Cancer*, 66(8) Cancer Research 3992-3995 (2006).
Lièvre et al., *KRAS Mutations As an Independent Prognostic Factor in Patients With Advance Colorectal Cancer Treated With Cetuximab*, 26(3) Journal of Clinical Oncology (Jan. 20, 2008).
Mimeault et al., *Pathobiological Implications of the Expresssion of EGFR, Pakt, Nf-kB and MIC-1 in Prostate Cancer Stem Cells and Their Progenies*, 7(2) PLos One 1-17 (Feb. 2012).
Mosakhani et al., *MicroRNA profiling predicts survival in anti-EGFR treated chemorefactory metastatic colorectal cancer patients with wild-type KRAS and BRAF*, 205 Cancer Genetics 545-551 (2012).
Mosakhani et al., *MicroRNA Profiling Differentiates Colorectal Cancer According to KRAS Status*, 51 Genes, Chromosomes & Cancer 1-9 (2012).
Pan et al., *Prognostic significance of expression of cyclooxygenase-2, vascular endothelial growth factor, and epidermal growth factor receptor in nasopharyngeal carcinoma*, 35(9) Head & Neck 1238-1247 (Sep. 2013).
Ragusa et al., *Specific Alterations of MicroRNA Transcriptome and Global Network Structure in Colorectal Carinoma after Cetuximab Treatment*, 9(12) Mol. Cancer Ther. 3396-3409 (2010).
Tam et al., *Distinct Epidermal Growth Factor Receptor and KRAS Mutation Patterns in Non-Small Cell Lung Cancer Patients with Different Tobacco Exposure and Clinicopathologic Features*, 12 Clin Cancer Res 1647-1653 (2006).
Thomasson et al., *LR1G1 and epidermal growth factor receptor in renal cell carcinoma: a quantitative RT-PCR and immunohistochemical analysis*, 89(7) British Journal of Cancer 1285-1289 (2003).
Thomasson et al., *Gene expression pattern of the epidermal growth factor receptor family and LRIG1 in renal cell carcinoma*, 5(216) BMC Research Notes 1-5 (2012).
Wheeler et al., *Understanding resistance to EGFR inhibitors—impact on future treatment strategies*, 7(9) Nat Rev Olin ONcol. 493-507 (Sep. 2010).
Xiao et al., *Upregulation of miR-31\* Is Negatively Associated with Recurrent/Newly Formed Oral Leukoplakia*, 7(6) PLoS One 1-10 (Jun. 2012).
Zeineldin et al., *Targeting the EGF Receptor for Ovarian Cancer Therapy*, 2010 Journal of Oncology 1-11 (Jun. 15, 2009).
Zhang et al., *A let-7 microRNA-binding site polymorphism in 3'-untranslated region of KRAS gene predicts response in wild-type KRAS patients with metastatic colorectal cancer treated with cetuximab monotherapy*, 22 Annals of Oncology 104-109 (2011) (online Jul. 5, 2010).
Zhao et al., *MiRNA expression analysis of cancer-associated fibroblasts and normal fibroblasts in breast cancer*, 44 The International Journal of Biochemistry & Cell Biology 2051-2059 (2012).
International Search Report dated Feb. 1, 2013, in PCT Application No. PCT/EP2012/073535.
Heinemann et al., *Clinical relevance of EGFR- and KRAS-status in colorectal cancer patients treated with monoclonal antibodies directed against the EGFR*, 35 Cancer Treatment Reviews 262-271 (2009).
Asnacios et al., *Gemcitabine Plus Oxaliplatin (GEMOX) Combined With Cetuximab in Patients With Progressing Advanced Stage Hepatocellular Carcinoma*, 112(12) Cancer 2733-2739 (Jun. 15, 2008).
Bansal et al., *The Molecular Bilogy of Endometrial Cancers and the Implications for Pathogenesis, Classification, and Targeted Therapies*, 16(1) Cancer Control 8-13 (Jan. 2009).
Belda-Iniesta et al., *Long term response with cetuximab therapy in glioblastoma multiform*, 5(8) Cancer Biology & Therapy 912-914 (Aug. 2006).
Ciardiello et al., *A Novel Approach in the Treatment of Cancer: Targeting the Epidermal Growth Factor Receptor*, 7 Clincal Cancer Research 2958-2970 (Oct. 2001).
Chan, *Nasopharyngeal carcinoma*, 21(Supplement 7) Annals of Oncology Vii308-vii312 (2010).

(56) References Cited

OTHER PUBLICATIONS

Cox et al., *Regression Models and Life-Tables*, 34(2) Journal of the Royal Statistical Society Series B (Methodological), 187-220 (1972).
Cunningham et al., *Cetuximab Monotherapy and Cetuximab plus Ironotecan in Ironotecan-Refractory Metastatic Colorectal Cancer*, 351 The New England Journal of Medicine 337-345 (2004).
Demiralay et al., *The Frequency of K-ras Mutation in Colorectal Adenocarcinomas with Absence of Distant Metastasis at Diagnosis*, 3 Surgical Science 111-115 (2012).
Eisenhauer et al., *New response evaluation criteria in solid tumours: Reviews RECIST guideline* (version 1.1), 45 European Journal of Cancer 228-247 (2009).
Lawrie et al., *Detection of elevated levels of tumour-associated microRNAs in serum of patients with diffuse large B-cell lymphoma*, British Journal of Haematology 672-675 (2008).
Mitchell et al., *Circulating micro RNAs as stable blood-based markers for cancer detection*, 105(30) PNAS 10513-10518 (Jul. 29, 2008).
Nobuhara et al., *Efficacy of epidermal growth factor receptor-targeted molecular therapy in anaplastic thyroid cancer cell lines*, 92 British Journal of Cancer 1110-1116 (2005).
Ogino et al., *Sensitive Sequencing Method for KRAS Mutation Detection by Pyrosequencing*, 7(3) Journal of Molecular Diagnostics 413-421 (Aug. 2005).
Philip et al., *Phase Ii Study of Erlotinib (OSI-774) in Patients With Advanced Hepatocellular Cancer*, 23(27) Journal of Clinical Oncology 6657-6663 (Sep. 20, 2005).
Reid et al., *Circulating microRNAs Association with disease and potential use as biomarkers*, 80 Critical Review in Oncology/Hematology 193-208 (2011).
Rich et al., *Phase II Trial of Gefitinib in Recurrent Gliobalstoma*, 22(1) Journal of Clinical Oncology 133-142 (Jan. 1, 2004).
Rosell et al., *Randomized phase II study of cetuximab plus cisplatin/vinorelbine compared with cisplatin/vinorelbine alone as first-line therapy in EGFR-expressing advanced non-small-cell lung cancer*, 19 Annals of Oncology 362-369 (2008).
Shepherd et al., *Erlotinib in Previously Treated Non-Small-Cell Lung Cancer*, 353(2) The New England Journal of Medicine 123-132 (2005).
Tsujiura et al., *Circulating microRNAs in plasma of patients with gastric cancers*, 102 British Journal of Cancer 1174-1179 (2010).

* cited by examiner

SEQUENCE LISTING

<160> NUMBER OF SEQ ID NOS: 3

<210> SEQ ID NO 1
<211> LENGTH: 22
<212> TYPE: RNA
<213> ORGANISM: homo sapiens

<400> SEQUENCE: 1
ugcuaugcca acauauugcc au                                              22

<210> SEQ ID NO 2
<211> LENGTH: 188
<212> TYPE: PRT
<213> ORGANISM: homo sapiens

<400> SEQUENCE: 2

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 3
<211> LENGTH: 766
<212> TYPE: PRT
<213> ORGANISM: homo sapiens

<400> SEQUENCE: 3

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
        50                  55                  60

Leu Asp Lys Phe Gly Gly Glu His Asn Pro Pro Ser Ile Tyr Leu Glu
65                  70                  75                  80

-continued

Ala Tyr Glu Glu Tyr Thr Ser Lys Leu Asp Ala Leu Gln Gln Arg Glu
             85                  90                  95

Gln Gln Leu Leu Glu Ser Leu Gly Asn Gly Thr Asp Phe Ser Val Ser
        100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn

```
                        500                 505                 510
Ile Leu Leu Phe Met Gly Tyr Ser Thr Lys Pro Gln Leu Ala Ile Val
            515                 520                 525

Thr Gln Trp Cys Glu Gly Ser Ser Leu Tyr His His Leu His Ile Ile
            530                 535             540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
                580                 585             590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
            610                 615             620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650             655

Ser Asn Ile Asn Asn Arg Asp Gln Ile Ile Phe Met Val Gly Arg Gly
                660                 665             670

Tyr Leu Ser Pro Asp Leu Ser Lys Val Arg Ser Asn Cys Pro Lys Ala
            675                 680             685

Met Lys Arg Leu Met Ala Glu Cys Leu Lys Lys Lys Arg Asp Glu Arg
            690             695             700

Pro Leu Phe Pro Gln Ile Leu Ala Ser Ile Glu Leu Leu Ala Arg Ser
705                 710             715                 720

Leu Pro Lys Ile His Arg Ser Ala Ser Glu Pro Ser Leu Asn Arg Ala
                725                 730             735

Gly Phe Gln Thr Glu Asp Phe Ser Leu Tyr Ala Cys Ala Ser Pro Lys
            740                 745             750

Thr Pro Ile Gln Ala Gly Gly Tyr Gly Ala Phe Pro Val His
            755                 760             765
```

METHOD FOR PREDICTING RESPONSIVENESS TO A TREATMENT WITH AN EGFR INHIBITOR

CROSS-REFERENCE TO RELATED APPLICATIONS

This application is a U.S. National Stage pursuant to 35 U.S.C. § 371 of International Patent Application PCT/EP2012/073535, filed on Nov. 23, 2012, and published as WO 2013/076282 on May 30, 2013, which claims priority to European Patent Application 12306042.8, filed on Aug. 31, 2012, and European Patent Application 11306568.4, filed on Nov. 25, 2011, all of which are incorporated herein by reference in their entireties for all purposes.

The present invention provides methods for individualizing chemotherapy for cancer treatment, and particularly for evaluating a patient's responsiveness to one or more epidermal growth factor receptor (EGFR) inhibitors prior to treatment with such agents.

BACKGROUND OF THE INVENTION

The proteasome plays a pivotal role in the turnover of regulatory transduction proteins induced by activated cell membrane growth factor receptors. The epidermal growth factor receptor (EGFR) pathway is crucial in the development and progression of human epithelial cancers. The combined treatment with EGFR inhibitors has a synergistic growth inhibitory and pro-apoptotic activity in different human cancer cells which possess a functional EGFR-dependent autocrine growth pathway through to a more efficient and sustained inhibition of Akt.

EGFR inhibitors have been approved or tested for treatment of a variety of cancers, including non-small cell lung cancer (NSCLC), head and neck cancer, colorectal carcinoma, and Her2-positive breast cancer, and are increasingly being added to standard therapy. EGFR inhibitors, which may target either the intracellular tyrosine kinase domain or the extracellular domain of the EGFR target, are generally plagued by low population response rates, leading to ineffective or non-optimal chemotherapy in many instances, as well as unnecessary drug toxicity and expense. For example, a reported clinical response rate for treatment of colorectal carcinoma with cetuximab (a chimeric monoclonal antibody targeting the extracellular domain of EGFR) is about 11% (Cunningham et al, N Engl Med 2004; 351: 337-45), and a reported clinical response rate for treatment of NSCLC with erlotinib is about 8.9% (Shepherd F A, et al, N Engl J Med 2005; 353:123-132).

In particular resistance has been observed in case of KRAS mutation.

In colorectal cancer, as KRAS mutations are clearly associated with resistance to anti-EGFR antibodies (Lievre et al, Cancer Res. 2006 66(8):3992-5), one of the major challenges is to identify, in non-mutated KRAS patients, other markers that can predict lack of response to this therapy. Among them, amplification or activating mutations of oncogenes and inactivating mutations of tumor suppressor genes described above are relevant candidates, such as the level of activation of EGFR downstream signaling pathway evaluated by the measurement of EGFR downstream phosphoprotein expression.

In lung cancer, three groups of patients are emerging: one counts the patients with EGFR mutated tumors for which the use of EGFR tyrosine kinase inhibitors (EGFR TKI) was proven to improve outcome, the second counts the patients with KRAS mutated tumors for which anti-EGFR therapies are probably not the good alternatives, and the third group counts the non-EGFR and non-KRAS mutated tumors for which response cannot be predicted. No marker linked to drug response in the non-mutated tumor group has proved valuable so far.

Thus, there is a need for predicting patient responsiveness to EGFR inhibitors prior to treatment with such agents, so as to better individualize patent therapy.

There are many documents in the prior art concerning the involvement of micro RNAs (miRNAs) in sensibility or resistance to various anticancer treatments. However, in most cases, studies are partial, incomplete, and actually do not permit a true prediction of clinical response or non-response to treatment. Indeed, in many cases, studies are limited to the analysis of the expression of miRNAs in vitro, in cell lines sensitive or resistant to a particular treatment, or in tumor cells isolated from a patient tumor. In addition, in many studies, while differences in expression level between two populations of cells or patients are shown, no threshold value or score actually permitting to predict response or non-response in a new patient are provided. This is partly linked to the first shortage that many studies lack data obtained in a clinical setting. Moreover, even when some data obtained in a clinical setting is presented, these data are most of the time only retrospective, and data validating a prediction method in a new cohort are often lacking.

As an example, WO2010/121238 describes the analysis of miRNAs expression in lung cancer cell lines sensitive or resistant to EGFR tyrosine kinase inhibitors cultures in vitro. No data obtained in a clinical setting is presented.

WO2009/080437 broadly claims methods for predicting response or non-response to anticancer treatment. However, data presented in WO2009/080437 is limited to various conventional chemotherapy treatments, and no data is provided concerning EGFR inhibitors (neither for anti-EGFR monoclonal antibodies nor for EGFR tyrosine kinase inhibitors). In addition, data presented for other chemotherapeutic molecules were obtained based on expression of miRNAs in tumor cells isolated from patient's tumors cultured in vitro. No data obtained in a clinical setting is presented.

Similarly, while WO2011/135459 broadly claims methods for predicting response or non-response to anticancer treatment, data presented in this document are limited to prediction of sensitivity or resistance of cancer cell lines to various anticancer agents in vitro. Here also, no data obtained in a clinical setting is presented, and thus no correlation between miRNA expression level and clinical response or survival of patient is demonstrated.

Ragusa et al-2010 (Ragusa M. et al. Mol Cancer Ther. 2010 December; 9(12):3396-409) analyzed the expression level of miRNAs after treatment with cetuximab in colorectal cancer cell lines known to be sensitive or resistant to cetuximab treatment. Two miRNAs are shown to be differentially expressed in KRAS wild-type versus KRAS mutated patients. However, differential expression in KRAS wild-type versus KRAS mutated patients does not permit to predict response to EGFR inhibitors in KRAS wild-type patients. In addition, as in many other studies, no data obtained in a clinical setting showing the ability of the expression levels of these miRNAs to independently predict response to EGFR inhibitors in patients is presented.

Hatakeyama et al-2010 (Hatakeyama H. et al. PLoS One. 2010 Sep. 13; 5(9):e12702) discloses the comparison of proteins activated in two cell lines derived from squamous cell carcinoma of the head and neck, one sensitive and the other resistant to cetuximab, after cetuximab treatment in vitro. An EGFR ligand, (HB-EGF or TGFA) is found in higher amount in the cetuximab resistant cell line. This protein is regulated by miR-22. In this study also, no data obtained in a clinical setting showing the ability of miR-22 expression level to predict response to cetuximab in patients is presented.

Therefore many studies lack clinical data showing that the expression level of a particular miRNA actually permits to discriminate between patients that clinically respond to the treatment (resulting in increased survival) and those with progressive disease and decreased survival. While data on cell lines or tumor cells in vitro may be considered as supporting further analysis for prediction of response or non-response in a clinical setting, it is clearly not sufficient to be considered as providing a true method for prediction of clinical response in patients. This is notably demonstrated by the fact that miRNAs found to be differentially expressed in sensitive versus resistant cell lines or tumor cells in vitro in the above mentioned documents were not found to be significantly correlated to clinical response (progression free survival or overall survival) in the clinical data analyzed in the present application.

There was thus a need for true and validated methods for predicting response to EGFR inhibitors in patients for which such therapy is one of several options. The present invention provides a response to this need.

SUMMARY OF THE INVENTION

The present invention provides an in vitro method for predicting whether a patient with a cancer is likely to respond to an epidermal growth factor receptor (EGFR) inhibitor, which comprises determining the expression level of hsa-miR-31-3p (previously named hsa-miR-31*, SEQ ID NO:1) miRNA in a sample of said patient.

Preferably the patient has a KRAS wild-type cancer.

The cancer preferably is a colorectal cancer, preferably a metastatic colorectal cancer.

In a most preferred embodiment, the invention provides an in vitro method for predicting whether a patient with a metastatic colorectal carcinoma is likely to respond to an epidermal growth factor receptor (EGFR) inhibitor, such as cetuximab or panitumumab, which method comprises determining the expression level of hsa-miR-31-3p (SEQ ID NO:1) miRNA in a tumor tissue sample of said patient.

The invention also provides a kit for determining whether a patient with a cancer is likely to respond to an epidermal growth factor receptor (EGFR) inhibitor, comprising or consisting of: reagents for determining the expression level of hsa-miR-31-3p (SEQ ID NO:1) miRNA in a sample of said patient, and reagents for determining the BRAF status of the patient.

The invention further relates to an EGFR inhibitor for use in treating a patient affected with a cancer, wherein the patient has been classified as being likely to respond, by the method according to the invention.

The invention also relates to the use of an EGFR inhibitor for the preparation of a drug intended for use in the treatment of cancer in patients that have been classified as "responder" by the method of the invention.

The invention also relates to a method for treating a patient affected with a cancer, which method comprises (i) determining whether the patient is likely to respond to an EGFR inhibitor, by the method of any of claims 1 to 15, and (ii) administering an EGFR inhibitor to said patient if the patient has been determined to be likely to respond to the EGFR inhibitor.

BRIEF DESCRIPTION OF THE FIGURES

FIG. 4A: groups 2+3 (38 patients), FIG. 4B: group 2 (19 patients treated with cetuximab), FIG. 4C: group 3 (19 patients treated with Panitumumab).

DETAILED DESCRIPTION OF THE INVENTION

Definitions

Figure 1:
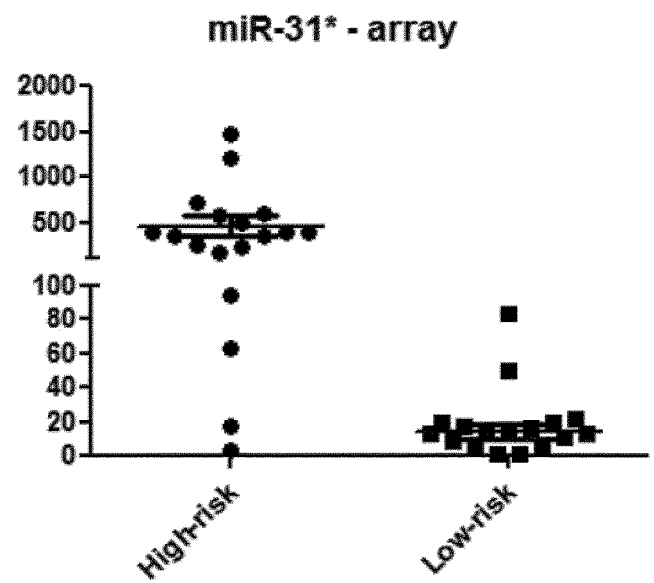
FIG. 1 is a graph that shows the expression level of hsa-miR-31-3p quantified by array (n=43; mean±SEM). Molecular weights are shown. P<0.0001.

The "patient" may be any mammal, preferably a human being, whatever its age or sex. The patient is afflicted with a cancer. The patient may be already subjected to a treatment, by any chemotherapeutic agent, or may be untreated yet.

The cancer is preferably a cancer in which the signaling pathway through EGFR is involved. In particular, it may be e.g. colorectal, lung, breast, ovarian, endometrial, thyroid, nasopharynx, prostate, head and neck, kidney, pancreas, bladder, or brain cancer (Ciardello F et al. N Engl J Med. 2008 Mar. 13; 358(11):1160-74; Wheeler D L et al. Nat Rev Clin Oncol. 2010 September; 7(9): 493-507; Zeineldin R et al. J Oncol. 2010; 2010:414676; Albitar L et al. Mol Cancer 2010; 9:166; Leslie K K et al. Gynecol Oncol. 2012 November; 127(2):345-50; Mimeault M et al. PLoS One. 2012; 7(2):e31919; Liebner D A et al. Ther Adv Endocrinol Metab. 2011 October; 2(5):173-95; Leboulleux S et al. Lancet Oncol. 2012 September; 13(9):897-905; Pan J et al. Head Neck. 2012 Sep. 13; Chan S L et al. Expert OpinTher Targets. 2012 March; 16 Suppl 1:S63-8; Chu H et al. Mutagenesis. 2012 Oct. 15; Li Y et al. Oncol Rep. 2010 October; 24(4):1019-28; Thomasson M et al. Br J Cancer 2003, 89:1285-1289; Thomasson M et al. BMC Res Notes. 2012 May 3; 5:216). In certain embodiments, the tumor is a solid tissue tumor and/or is epithelial in nature. For example, the patient may be a colorectal carcinoma patient, aHer2-positiveor Her2-negative (in particular triple negative, i.e. Her2-negative, estrogen receptor negative and progesterone receptor negative) breast cancer patient, a non-small cell lung cancer (NSCLC) patient, a head and neck cancer patient (in particular a squamous-cell carcinoma of the head and neck patient), a pancreatic cancer patient, or an endometrial cancer patient. More particularly, the patient may be a colorectal carcinoma patient, a Her2-positive or Her2-negative (in particular triple negative) breast cancer patient, a lung cancer (in particular a NSCLC) patient, a head and neck cancer patient (in particular a squamous-cell carcinoma of the head and neck patient), or a pancreatic cancer patient.

In a preferred embodiment, the cancer is a colorectal cancer, still preferably the cancer is a metastatic colorectal cancer. Indeed, data presented in Examples 1-3, as well as those disclosed in Mosakhani et al-2012 (Mosakhani N. et al. Cancer Genet. 2012 Oct. 22. doi:pii: S2210-7762(12) 00229-3. 10.1016/j.cancergen.2012.08.003), clearly indicate that hsa-miR-31-3p expression level may be used as a predictor of response to EGFR inhibitors (and in particular to anti-EGFR monoclonal antibodies such as cetuximab and panitumumab) treatment in colorectal cancer.

These results, obtained in a cancer in which the EGFR signaling pathway is known to be involved, clearly suggest that hsa-miR-31-3p expression level might be used as a predictor of response to EGFR inhibitors (and in particular to anti-EGFR monoclonal antibodies such as cetuximab and panitumumab) in any other cancer in which the EGFR signaling pathway is known to be involved, such as lung, ovarian, endometrial, thyroid, nasopharynx, prostate, head and neck, kidney, pancreas, bladder, or brain cancer. This is particularly true because hsa-miR-31-3p has been shown to be overexpressed in some of these other cancers (see Chang K W et al. Oral Oncol. 2012 Jul. 30, Xiao W et al. 2012. PLoS ONE 7(6): e38648, and Zhao L. et al. Int J Biochem Cell Biol. 2012 November; 44(11):2051-9). Since hsa-miR-31-3p is correlated to response to EGFR inhibitors and thus to EGFR signaling pathway and since it is expressed in several cancers in which EGFR signaling pathway is known to be involved, it can be reasonably expected to be useful in prediction of response to EGFR inhibitors (and in particular to anti-EGFR monoclonal antibodies such as cetuximab and panitumumab) in any other cancer in which the EGFR signaling pathway is known to be involved.

In another preferred embodiment, the cancer is a Her2-positive or Her2-negative (in particular triple negative) breast cancer, preferably a Her2-negative (in particular triple negative) breast cancer.

In still another preferred embodiment, the cancer is a lung cancer, in particular a non-small cell lung cancer (NSCLC).

In still another preferred embodiment, the cancer is a pancreatic cancer.

Obviously, since the prediction relates to EGFR inhibitors treatment, the patient's tumor is preferably EGFR positive.

Preferably, the patient has a KRAS wild-type tumor, i.e., the KRAS gene in the tumor of the patient is not mutated in codon 12, 13 (exon 1), or 61 (exon 3). In other words, the KRAS gene is wild-type on codons 12, 13 and 61.

Wild type, i.e. non mutated, codons 12, 13 (exon 1), and 61 (exon 3) respectively correspond to glycine (Gly, codon 12), glycine (Gly, codon 13), and glutamine (Gln, codon 61). The wild-type reference KRAS amino acid sequence may be found in Genbank accession number NP_004976.2 (SEQ ID NO:2).

Especially the KRAS gene of the patient's tumor does not show any of the following mutations (Bos. Cancer Res 1989; 49:4682-4689; Edkins et al. Cancer Biol Ther. 2006 August; 5(8): 928-932; Demiralay et al. Surgical Science, 2012, 3, 111-115):

Gly12Ser (GGT>AGT)
Gly12Arg (GGT>CGT)
Gly12Cys (GGT>TGT)
Gly12Asp (GGT>GAT)
Gly12Ala (GGT>GCT)
Gly12Val (GGT>GTT)
Gly13Arg (GGC>CGC)
Gly13Cys (GGC>TGC)

Gly13Asp (GGC>GAC)
Gly13Ala (GGC>GCC)
Gly13Val (GGC>GTC)

Preferably, the KRAS gene of the patient's tumor does also not show any of the following mutations (Demiralay et al. Surgical Science, 2012, 3, 111-115):
Gly12Phe (GGT>TTT)
Gly13Ser (GGC>AGC)

Preferably, the KRAS gene of the patient's tumor does also not show any of the following mutations (Bos. Cancer Res 1989; 49:4682-4689; Tam et al. Clin Cancer Res 2006; 12:1647-1653; Edkins et al. Cancer Biol Ther. 2006 August; 5(8): 928-932; Demiralay et al. Surgical Science, 2012, 3, 111-115):
Gln61His (CAA>CAC)
Gln61His (CAA>CAT)
Gln61Arg (CAA>CGA)
Gln61Leu (CAA>CTA)
Gln61Glu (CAA>GAA)
Gln61Lys (CAA>AAA)
Gln61Pro (CAA>CCA)

Any method known in the art may be used to know the KRAS status of the patient.

For example, a tumor tissue is microdissected and DNA extracted from paraffin-embedded tissue blocks. Regions covering codons 12, 13, and 61 of the KRAS gene are amplified using polymerase chain reaction (PCR). Mutation status is determined by allelic discrimination using PCR probes (Laurent-Puig P, et al, J Clin Oncol. 2009, 27(35): 5924-30) or by any other methods such as pyrosequencing (Ogino S, et al. J Mol Diagn 2008; 7:413-21).

The "sample" may be any biological sample derived from a patient, which contains nucleic acids. Examples of such samples include fluids (including blood, plasma, saliva, urine, seminal fluid), tissues, cell samples, organs, biopsies, etc. Preferably the sample is a tumor sample, preferably a tumor tissue biopsy or whole or part of a tumor surgical resection. The sample may be collected according to conventional techniques and used directly for diagnosis or stored. A tumor sample may be fresh, frozen or paraffin-embedded. Usually, available tumor samples are frozen or paraffin-embedded, most of the time paraffin-embedded. The inventors have shown that both frozen and paraffin-embedded tumor samples may be used.

By a "reference sample", it is meant a tumor sample (notably a tumor biopsy or whole or part of a tumor surgical resection) of a patient whose positive or negative response to an EGFR inhibitor treatment is known. Preferably, a pool of reference samples comprises at least one (preferably several, more preferably at least 5, more preferably at least 6, at least 7, at least 8, at least 9, at least 10) responder patient(s) and at least one (preferably several, more preferably at least 6, at least 7, at least 8, at least 9, at least 10) non responder patient(s). The highest the number of responders (also referred to as "positive") and non responders (also referred to as "negative") reference samples, the better for the reliability of the method of prediction according to the invention.

Within the context of this invention, a patient is "likely to respond" or is "responder" refers to a patient who may respond to a treatment with an anti-EGFR inhibitor, i.e. least one of his symptoms is expected to be alleviated, or the development of the disease is stopped, or slowed down. Complete responders, partial responders, or stable patients according to the RECIST criteria (Eisenhauer et al, European Journal of Cancer, 2009, 45:228-247) are considered as "likely to respond" or "responder" in the context of the present invention.

In solid tumors, the RECIST criteria are an international standard based on the presence of at least one measurable lesion. "Complete response" means disappearance of all target lesions; "partial response" means 30% decrease in the sum of the longest diameter of target lesions, "progressive disease" means 20% increase in the sum of the longest diameter of target lesions, "stable disease" means changes that do not meet above criteria.

More preferably, a "responder" patient is predicted to show a good progression free survival (PFS), i.e. the patient is likely to survive at least 25 weeks without aggravation of the symptoms of the disease, and/or such patient shows a good overall survival (OS), i.e. the patient is likely to survive at least 14 months.

The term "predicting" or "prognosis" refers to a probability or likelihood for a patient to respond to the treatment with an EGFR inhibitor.

According to the invention, the sensitivity of tumor cell growth to inhibition by an EGFR inhibitor is predicted by whether such tumor cells express hsa-miR-31-3p miRNA.

The term "treating" or "treatment" means stabilizing, alleviating, curing, or reducing the progression of the cancer.

A "miRNA" or "microRNA" is a single-stranded molecule of about 21-24 nucleotides, preferably 21-23 in length, encoded by genes that are transcribed from DNA but not translated into protein (non-coding RNA); instead they are processed from primary transcripts known as pri-miRNA to short stem-loop structures called pre-miRNA and finally to functional miRNA. During maturation, each pre-miRNA gives rise to two distinct fragments with high complementarity, one originating from the 5' arm the other originating from the 3' arm of the gene encoding the pri-miRNA. Mature miRNA molecules are partially complementary to one or more messenger RNA (mRNA) molecules, and their main function is to downregulate gene expression.

There is an international nomenclature of miRNAs (see Ambros V et al, RNA 2003 9(3):277-279; Griffiths-Jones S. NAR 2004 32(Database Issue):D109-D111; Griffiths-Jones S et al. NAR 2006 34(Database Issue):D140-D144; Griffiths-Jones S et al. NAR 2008 36(Database Issue):D154-D158; and Kozomara A et al. NAR 2011 39(Database Issue):D152-D157), which is available from miRBase. Each miRNA is assigned a unique name with a predefined format, as follows:

For a mature miRNA: sss-miR-X-Y, wherein"
  sss is a three letters code indicating the species of the miRNA, "has" standing for human,
  the upper case "R" in miR indicates that it is referred to a mature miRNA. However, some authors in the literature abusively use "mir" also for mature miRNA. In this case, it may be recognized that it is referred to a mature miRNA by the presence of "-Y",
  X is the unique arbitrary number assigned to the sequence of the miRNA in the particular species, which may be followed by a letter if several highly homologous miRNAs are known. For instance, "20a" and "20b" refer to highly homologous miRNAs.
  Y indicates whether the mature miRNA, which has been obtained by cutting of the pre-miRNA, corresponds to the 5' arm (Y is then "5p") or 3' arm (Y is then "3p") of the gene encoding the pri-mRNA. In previous international nomenclature of miRNAs, "-Y" was not present. The two mature miRNAs obtained either from the 5' or the 3' arm of the gene encoding the pri-miRNA were then distinguished by the presence or absence of a "*" sign just after n. The presence of the "*" sign indicated that the sequence corresponded to the less often detected miRNA. Since such classification was subject to changes, a new nomenclature using the "3p" and "5p" code has been implemented.

For a pri-miRNA:sss-mir-X, wherein sss is a three letters code indicating the species of the miRNA, "has" standing for human, the lower case "r" in mir indicates that it is referred to a pri-miRNA and not to a mature miRNA, which is confirmed by the absence of "-Y", n is the unique arbitrary number assigned to the sequence of the miRNA in the particular species, which may be followed by a letter if several highly homologous miRNAs are known.

Each miRNA is also assigned an accession number for its sequence.

The miRNA detected in the present invention is hsa-miR-31-3p (previously named hsa-miR-31*). In this name, "hsa" means that it relates to a human miRNA, "miR" refers to a mature miRNA, "31" refers to the arbitrary number assigned to this particular miRNA, and "3p" means that the mature miRNAs has been obtained from the 3' arm of the gene encoding the pri-miRNA.

```
miR-31-3p is
                                    (SEQ ID NO : 1)
UGCUAUGCCAACAUAUUGCCAU
(Accession number MIMAT0004504)
```

Methods of Detecting miRNA Levels in a Sample

The expression level of the miRNAs may be determined, e.g. the miRNAs may be quantified, by methods known by anyone skilled in the art. In particular, real time quantitative RT-PCR (qRT-PCR) may be useful.

Nucleic acid assays or arrays can also be used to assess the levels of the miRNAs in a sample.

In some embodiments, an oligonucleotide array can be prepared or purchased. An array typically contains a solid support and at least one oligonucleotide contacting the support, where the oligonucleotide corresponds to at least a portion of a miRNA.

Any suitable assay platform can be used to determine the presence of the miRNA in a sample. For example, an assay may be in the form of a membrane, a chip, a disk, a test strip, a filter, a microsphere, a multiwell plate, and the like. An assay system may have a solid support on which an oligonucleotide corresponding to the miRNA is attached. The solid support may comprise, for example, a plastic, silicon, a metal, a resin, or a glass. The assay components can be prepared and packaged together as a kit for detecting an miRNA.

In some embodiments, qRT-PCR can be used for both the detection and quantification of RNA targets (Bustin et al., 2005, Clin. Sci., 109:365-379). Quantitative results obtained by qRT-PCR can sometimes be more informative than qualitative data, and can simplify assay standardization and quality management. Thus, in some embodiments, qRT-PCR-based assays can be useful to measure miRNA levels during cell-based assays. The qRT-PCR method may be also useful in monitoring patient therapy. Examples of qRT-PCR-based methods can be found, for example, in U.S. Pat. No. 7,101,663. Commercially available qRT-PCR based methods (e.g., Taqman® Array). Human miRNA panel from Applied Biosystems may also be employed.

In another embodiment, the miRNA quantification may be performed by sequencing.

Classifying the Patient

The lower the expression of hsa-miR-31-3p is, the better for the patient. Therefore, the lower the level of expression of the miRNA is, the more likely the patient is to respond to the EGFR inhibitor treatment. In an embodiment, the patient is considered as "responder", or likely to respond to a treatment with an EGFR inhibitor, when the expression of hsa-miR-31-3p is lower than a control value.

Such a control value may be determined based on a pool of reference samples, as defined above. In particular, FIG. 1 and FIG. 2A clearly show that, based on a pool of reference samples, a control value for hsa-miR-31-3p level of expression (the logged hsa-miR-31-3p level of expression) may be defined that permits to predict response or non-response to EGFR inhibitor treatment.

However, in a preferred embodiment, the method further comprises determining a prognostic score or index based on the expression level of the miRNA, wherein the prognostic score indicates whether the patient is likely to respond to the EGFR inhibitor. In particular, said prognosis score may indicate whether the patient is likely to respond to the EGFR inhibitor depending if it is higher or lower than a predetermined threshold value (dichotomized result). In another embodiment, a discrete probability of response or non response to the EGFR inhibitor may be derived from the prognosis score.

The probability that a patient responds to an EGFR inhibitor treatment is linked to the probability that this patient survives, with or without disease progression, if the EGFR inhibitor treatment is administered to said patient.

As a result, a prognosis score may be determined based on the analysis of the correlation between the expression level of hsa-miR-31-3p and progression free survival (PFS) or overall survival (OS) of a pool of reference samples, as defined above. A PFS and/or OS score, which is a function correlating PFS or OS to the expression level of hsa-miR-31-3p, may thus be used as prognosis score for prediction of response to an EGFR inhibitor. Preferably, a PFS score is used, since absence of disease progression is a clear indicator of response to the EGFR inhibitor treatment.

In a preferred embodiment, a prognostic score is one of those determined as shown in the Example section:

The prognostic score can be computed by the following formulae (determined based on a pool of 22 reference samples as disclosed in Example 1):

PFS score=$0.203738*x-1.453362$ wherein $x$ is the logged expression of hsa-miR-31-3p.

OS score=$0.190677*x-1.360191$ wherein $x$ is the logged expression of hsa-miR-31-3p.

The patient is then predicted to be a responder if his/her prognostic score is lower than or equal to $-0.098088$ (PFS) and/or $-0.0918$ (OS). Preferably the patient is classified as a responder if his/her prognostic score is lower than or equal to $-0.098088$ (PFS).

In another embodiment, the prognostic score can be computed by the following formulae (determined based on a pool of 33 reference samples as disclosed in Example 2):

PFS score=$0.178366*x-1.363693$ wherein $x$ is the logged expression of hsa-miR31-3p.

OS score=$0.102142*x-0.780927$ wherein $x$ is the logged expression of hsa-miR31-3p.

The patient is then predicted to be a responder if his/her prognostic score is lower than or equal to −0.03123 (PFS) and/or −0.017884 (OS). Preferably the patient is classified as a responder if his/her prognostic score is lower than or equal to −0.03123 (PFS).

The PFS and OS scores determined in the experimental section have been obtained based on pools of 23 and 33 reference samples, which explains a minor variation between parameters of the linear function correlating PFS to the logged expression level of hsa-miR-31-3p in PFS scores determined in Examples 1 and 2. While some further minor variation in these parameters might occur upon inclusion of further reference samples, results obtained by the inventor confirm the existence of a linear correlation between survival (PFS or OS) and the logged expression of hsa-miR-31-3p in patient's tumor sample. Therefore, it can be concluded from the experimental data obtained by the inventors that the probability for a patient to respond to an EGFR inhibitor treatment is linearly correlated to the logged expression level of hsa-miR-31-3p. In a preferred embodiment, said prognosis score is thus represented by the following formula:

Prognosis score=a*x+b, wherein x is the logged expression level of hsa-miR-31-3p measured in the patient's sample, and a and b are parameters that have been previously determined based on a pool of reference samples, as defined above.

The patient may then be predicted as responding to the EGFR inhibitor if his/her prognosis score is lower than or equal to a threshold value c, and not responding to the EGFR inhibitor if his/her prognosis score is greater than threshold value c, wherein the value of c has also been determined based on the same pool of reference samples.

Based on the experiments performed by the inventors, it has been determined that, in this case, a, b and c are preferably in the following ranges:

a: [0.1; 0.25], preferably [0.17; 0.21];
b: [−2; −0.5], preferably [−1.8; −0.6], preferably [−1.5; −0.7]; and
c: [−0.11; −0.01], preferably [−0.10; −0.01]. Preferably, if a PFS score is used, c is in the range [−0.10; −0.03], and if an OS score is used, c is in the range [−0.1: −0.015].

In another embodiment, a discrete probability of response or non response to the EGFR inhibitor may be derived from the above a*x+b prognosis score. The lower the prognosis score, the higher is the probability of response to the EGFR inhibitor treatment. A precise correlation between the prognosis score and the probability of response to the EGFR inhibitor treatment may be determined based on the same set of reference samples.

The inventors also determined that, although response to EGFR inhibitors can be predicted based only on the expression level of hsa-miR-31-3p (see Examples 1 and 2), an even more reliable prediction can be made if a combination of hsa-miR-31-3p expression level and BRAF status is taken into account (see Example 2). Therefore, in a preferred embodiment, the method according to the invention further comprises determining the BRAF status of said patient, and calculating a composite score taking into account the expression level of hsa-miR-31-3p and the BRAF status, wherein the composite score indicates whether the patient is likely to respond to the EGFR inhibitor. BRAF gene is also referred to as proto-oncogene B-Raf and v-Raf murine sarcoma viral oncogene homolog B1, while the protein is more formally known as serine/threonine-protein kinase B-Raf. This protein plays a role in regulating the MAP kinase/ERKs signaling pathway, which affects cell division, differentiation, and secretion. Mutations in this gene have been associated with various cancers, including non-Hodgkin lymphoma, colorectal cancer, malignant melanoma, thyroid carcinoma, non-small cell lung carcinoma, and adenocarcinoma of lung.

The "BRAF status" is defined either as wild-type or mutated, depending on whether the BRAF protein of the patient's tumor comprises or not a V600E mutation (substitution of valine by glutamic acid in codon 600) compared to the wild type BRAF protein sequence defined by accession number NP_004324.2 (SEQ ID NO:3). The BRAF status is considered as "BRAF wild-type" if the BRAF protein does not comprise the V600E mutation compared to protein sequence NP_004324.2. In contrast, if the BRAF protein in the patient's tumor comprises the V600E mutation compared to protein sequence NP_004324.2, then the BRAF status is defined as "BRAF mutated".

BRAF status can be determined on tumor sample, preferably before the treatment with an EGFR inhibitor, by an allelic discrimination assay (as described in Laurent-Puig P, et al, J Clin Oncol. 2009, 27(35):5924-30 and Lievre et al. J Clin Oncol. 2008 Jan. 20; 26(3):374-9) or by direct sequencing, for instance.

The composite score may further comprise additional parameters associated to prediction of the response to the EGFR inhibitor. Such additional parameters may for instance include age and gender.

The composite score may notably be based on a nomogram, in which points scales are established for each variable of the composite score. For a given patient, points are allocated to each of the variables by selecting the corresponding points from the points scale of each variable. For a discrete variable (such as hsa-miR-31-3p expression level or age), the number of points attributed to a variable is linearly correlated to the value of the variable. For a dichotomized variable (only two values possible, such as BRAF mutation status or gender), two distinct values are attributed to each of the two possible values or the variable.

A composite score is then calculated by adding the points allocated for each variable. Based on the value of the composite score, the patient may then be given either a good or bad response prognosis depending on whether the composite score is inferior or superior to a threshold value (dichotomized score), or a probability of response or non response to the treatment.

The points scale of each variable, as well the threshold value over/under which the response prognosis is good or bad or the correlation between the composite score and the probability of response or non response may be determined based on the same pool of reference samples.

Specific examples of such composite scores are given in Example 2 (see also FIG. 6B and FIG. 7B), and correspond to preferred embodiments of the invention.

EGFR Inhibitors

The present invention makes it possible to predict a patient's responsiveness to one or more epidermal growth factor receptor (EGFR) inhibitors prior to treatment with such agents.

The EGRF inhibitor may be an EGFR tyrosine kinase inhibitor, or may alternatively target the extracellular domain of the EGFR target.

Preferably the EGFR inhibitor is an anti-EGFR antibody, preferably a monoclonal antibody.

In certain embodiments, the EGFR inhibitor is a tyrosine kinase inhibitor such as Erlotinib, Gefitinib, or Lapatinib, or a molecule that targets the EGFR extracellular domain such as Cetuximab or Panitumumab.

Molecules that target the EGFR extracellular domain, including anti-EGFR monoclonal antibodies such as Cetuximab or Panitumumab, are mainly used in the treatment of colorectal cancer or breast cancer treatment. As a result, if the patient's cancer is colorectal cancer (in particular metastatic colorectal cancer) or breast cancer, then the method according to the invention may preferably be used to predict response to molecules that target the EGFR extracellular domain, and in particular to anti-EGFR monoclonal antibodies, such as Cetuximab or Panitumumab.

Conversely, tyrosine kinase EGFR inhibitors are mainly used in the treatment of lung cancer (in particular non small cell lung cancer, NSCLC), so that if the patient's cancer is lung cancer (in particular non small cell lung cancer, NSCLC), then the method according to the invention may preferably be used to predict response to tyrosine kinase EGFR inhibitors, such as Erlotinib, Gefitinib, or Lapatinib.

In pancreatic cancer or head and neck cancer (in particular squamous cell carcinoma of the head and neck (SCCHN)), both tyrosine kinase EGFR inhibitors and anti-EGFR monoclonal antibodies are being tested as therapy, so that if the patient's cancer is pancreatic cancer or head and neck cancer (in particular squamous cell carcinoma of the head and neck (SCCHN)), then the method according to the invention may be used to predict response either to tyrosine kinase EGFR inhibitors (such as Erlotinib, Gefitinib, or Lapatinib) or to anti-EGFR monoclonal antibodies (such as Cetuximab or Panitumumab).

Cetuximab and Panitumumab are currently the clinically mostly used anti-EGFR monoclonal antibodies. However, further anti-EGFR monoclonal antibodies are in development, such as Nimotuzumab (TheraCIM-h-R3), Matuzumab (EMD 72000), and Zalutumumab (HuMax-EGFr). The method according to the invention may also be used to predict response to these anti-EGFR monoclonal antibodies or any other anti-EGFR monoclonal antibodies (including fragments) that might be further developed, in particular if the patient is suffering from colorectal cancer (in particular metastatic colorectal cancer), breast cancer, pancreatic cancer or head and neck cancer (in particular squamous cell carcinoma of the head and neck (SCCHN)).

Similarly, Erlotinib, Gefitinib, and Lapatinib are currently the clinically mostly used tyrosine kinase EGFR inhibitors. However, further tyrosine kinase EGFR inhibitors are in development, such as Canertinib (CI-1033), Neratinib (HKI-272), Afatinib (BIBW2992), Dacomitinib (PF299804,PF-00299804), TAK-285, AST-1306, ARRY334543, AG-1478 (Tyrphostin AG-1478), AV-412, OSI-420 (DesmethylErlotinib), AZD8931, AEE788 (NVP-AEE788), Pelitinib (EKB-569), CUDC-101, AG 490, PD153035 HCl, XL647, and BMS-599626 (AC480). The method according to the invention may also be used to predict response to these tyrosine kinase EGFR inhibitors or any other tyrosine kinase EGFR inhibitors that might be further developed, in particular if the patient is suffering from of lung cancer (in particular non small cell lung cancer, NSCLC), pancreatic cancer, or head and neck cancer (in particular squamous cell carcinoma of the head and neck (SCCHN)).

Kits

The present invention also relates to a kit for determining whether a patient with a cancer is likely to respond to an epidermal growth factor receptor (EGFR) inhibitor, comprising or consisting of:
 a) reagents for determining the expression level of hsa-miR-31-3p (SEQ ID NO:1) miRNA in a sample (preferably a tumor sample, such as a tumor biopsy or whole or part of a tumor surgical resection) of said patient, and
 b) reagents for determining the BRAF status of the patient.

Reagents for determining the expression level of hsa-miR-31-3p (SEQ ID NO:1) miRNA in a sample of said patient may notably include primers pairs (forward and reverse primers) and/or probes specific for hsa-miR-31-3p (SEQ ID NO:1) miRNA or a miRNA microarray comprising a sequence specific for hsa-miR-31-3p (SEQ ID NO:1) miRNA.

Reagents for determining the BRAF status of the patient may include at least one primer pair for amplifying whole or part of the BRAF gene before sequencing or a set of specific probes labeled with fluorescence reporter dyes FAM and VIC at their 5' end, for use in an allelic discrimination assay, for instance on an ABI 7900HT Sequence Detection System (Applied Biosystems, Foster City, Calif.) (see Laurent-Puig P, et al, J Clin Oncol. 2009, 27(35):5924-30 and Lievre et al. J Clin Oncol. 2008 Jan. 20; 26(3):374-9).

The kit of the invention may further comprise instructions for determining whether the patient is likely to respond to the EGFR inhibitor based on hsa-miR-31-3p (SEQ ID NO:1) miRNA expression level and BRAF status, and optionally further additional parameters. In particular, a nomogram including points scales of all variables included in the composite score and correlation between the composite score (total number of points) and the prediction (response/non response or probability of response or non response), as presented in FIGS. 5B and 6B, may be included.

Medicaments, Therapeutic Uses and Methods of Treating

The method of the invention predicts patient responsiveness to EGFR inhibitors at rates that match reported clinical response rates for the EGFR inhibitors.

It is thus further provided a method for treating a patient with a cancer, which method comprises administering the patient with at least one EGFR inhibitor, wherein the patient has been classified as "responder" by the method as described above.

In particular, the invention concerns a method for treating a patient affected with a cancer, which method comprises (i) determining whether the patient is likely to respond to an EGFR inhibitor, by the method according to the invention, and (ii) administering an EGFR inhibitor to said patient if the patient has been determined to be likely to respond to the EGFR inhibitor.

The method may further comprise, if the patient has been determined to be unlikely to respond to the EGFR inhibitor a step (iii) of administering an alternative anticancer treatment to the patient. Such alternative anticancer treatment depends on the specific cancer and on previously tested treatments, but may notably be selected from radiotherapy, other chemotherapeutic molecules, or other biologics such as monoclonal antibodies directed to other antigens (anti-Her2, anti-VEGF, anti-EPCAM, anti-CTLA4 . . . ). In particular, in the case of colorectal cancer, if the patient has been determined to be unlikely to respond to the EGFR inhibitor, the alternative anticancer treatment administered in step (iii) may be selected from:
 a VEGF inhibitor, in particular an anti-VEGF monoclonal antibodies (such as bevacizumab), advantageously in combination with FOLFOX (a combination of leucovorin (folinic acid), 5-fluorouracil (5-FU), and oxaliplatin) or FOLFIRI (a combination of leucovorin (folinic acid), 5-fluorouracil (5-FU), and irinotecan) chemotherapy.
 Alternatively, if the patient has already been treated unsuccessfully with a VEGF inhibitor, optionally in combination with FOLFOX or FOLFIRI chemotherapy, it may be administered with 5-FU, optionally in combination with Mitomycin B. Best supportive care, defined as a treatment administered with the intent to maximize quality of life without a specific antineoplastic regimen (i.e. not an anticancer treatment) may further be administered to the patient.

Another subject of the invention is an EGFR inhibitor, for use in treating a patient affected with a cancer, wherein the patient has been classified as being likely to respond, by the method as defined above. Said patient may be affected with a colorectal cancer, more particularly a metastatic colorectal cancer. Alternatively, said patient may be affected with a breast cancer, in particular a triple negative breast cancer. Alternatively, said patient may be affected with a lung cancer, in particular a non small cell lung cancer (NSCLC). Alternatively, said patient may be affected with a head and neck cancer, in particular a squamous-cell carcinoma of the head and neck. Alternatively, said patient may be affected with a pancreatic cancer. The invention also relates to the use of an EGFR inhibitor for the preparation of a medicament intended for use in the treatment of cancer in patients that have been classified as "responder" by the method of the invention as described above.

In a preferred embodiment the EGFR inhibitor is an anti-EGFR antibody, preferably cetuximab or panitumumab. Alternatively, the EGFR inhibitor may be a tyrosine kinase EGFR inhibitor, in particular Erlotinib, Gefitinib, or Lapatinib.

In preferred embodiments:
- the patient is afflicted with a colorectal cancer, in particular a metastatic colorectal cancer, and the EGFR inhibitor is an anti-EGFR antibody, preferably cetuximab or panitumumab;
- the patient is afflicted with a breast cancer, in particular a triple negative breast cancer, and the EGFR inhibitor is an anti-EGFR antibody, preferably cetuximab or panitumumab;
- the patient is afflicted with a lung cancer, in particular a non small cell lung cancer (NSCLC), and the EGFR inhibitor is a tyrosine kinase EGFR inhibitor, in particular Erlotinib, Gefitinib, or Lapatinib;
- the patient is afflicted with a head and neck cancer, in particular a squamous-cell carcinoma of the head and neck, or a pancreatic cancer, and the EGFR inhibitor is an anti-EGFR antibody (preferably cetuximab or panitumumab) or a tyrosine kinase EGFR inhibitor (in particular Erlotinib, Gefitinib, or Lapatinib).

The examples and figures illustrate the invention without limiting its scope.

EXAMPLES

Example 1

Levels of a miRNA in KRAS-wild-type Colorectal Carcinomas Determine Survival Differences in Patients Treated with Anti-EGFR Patients and Methods
Sets of Patients The first set of patients (herein named "discovery set") was composed of 43 patients, 29 males, 14 females. The median of age was 61.3±11.4 years. All had a metastatic disease at the time of the inclusion in this study. All these patients developed a KRAS wild type colon cancer.

The KRAS status was determined as follows. For each patient, a fragment of the tumor was frozen immediately after surgery. The DNA was extracted from tumor tissues with a Qiagen kit according to the manufacturer recommendation after a verification of the percentage of tumor cells in the tumor fragment (only fragments containing more than 50% of tumor cells were selected for DNA extraction and RNA extraction). The KRAS status has been checked in extracted tumor DNA using Taqman probes on codons 12 and 13 according to the method reported in Laurent-Puig P, et al, J Clin Oncol. 2009, 27(35):5924-30. The mutations on codon 61 were detected by exon 3 sequencing of the KRAS gene. All tumors selected in this first set group were KRAS wild-type on codons 12, 13 and 61. The response status of the patients was assessed according to RECIST criteria. Two patients were considered as complete responders, 12 as partial responders, 17 were considered with a stable disease, 12 were progressive at the first evaluation. Thirty-four patients had a documented progression during the follow-up and 31 patients died during the follow-up.

The median of follow-up until progression was 16.14 weeks and the median overall survival was 12.4 months. All the patients but 2 were refractory to Irinotecan, 2 were refractory to oxaliplatin; 33 receive combination of Cetuximab and Irinotecan, 1 a combination of Panitumumab and Irinotecan, 6 combination of Cetuximab plus FOLFIRI, 2 the combination of Cetuximab and FOLFOX and 1 the combination of Cetuximab and XELODA. The number of line of chemotherapy before the introduction of Cetuximab and panitumumab was recorded.

Quantification of miRNA Expression Levels

Small RNAs were extracted from frozen tumors of a subgroup of 23 patients, using the mirVanamiRNA Isolation Kit from Ambion. Global microRNA (miRNA) profiling was performed by labeling and hybridizing 750 ng of extracted RNA from each sample on Illumina Human v2 microRNA Expression Beadchips according to the manufacturer's recommendations. Beadchips were scanned with the Illuminai Scan Reader and data were imported into GenomeStudio (Illumina), quantile-normalized and $\log_2$-transformed. Specific quantification of expression level of miRNA hsa-miR-31-3p was performed using specific TaqMan pre-designed assays on ng of retrotranscribed RNA and a ABI7900HT Real-Time PCR System. Expression levels were normalized to the reference snRNA RNU6B levels through the $\Delta\Delta$Ct method.

Statistical Analysis

Statistical analyses were performed using GraphPad Prism software. Quantitative real time PCR expression data were presented as mean±SEM (standard error of the mean). Non-parametric Mann Whitney (MW) test was used to compare quantitative values. All reported p-values were two-tailed.

Survival Model Prediction

A microRNA expression-based predictor of survival risk group was calculated by combining a Cox proportional hazards model [Cox, D. R. (1972). Regression models and life-tables. Journal of the Royal Statistical Society, Series B 34 (2), 187-220] and a supervised principal component method [E Bair & R Tibshirani, Semi-supervised methods to predict patient survival from gene expression data, PLOS Biology 2:511-522, 2004)]. Univariate Cox proportional hazards model was used to categorize miRNAs for which log expression level is correlated with survival time. The hypothesis that the survival time is independent of the expression level was tested and the proportion of false discoveries was checked using multivariate permutation tests (N=1000, p<0.05). After selection of the miRNAs, principal components were computed and a Cox proportional hazard regression analysis was performed providing a regression coefficient (weight) for each principal component.

A composite prognostic score was calculated for a patient whose expression profile is described by a vector x of log expression levels combining the components of x with the weighted average of each principal component value. A high value of the prognostic score corresponds to a high value of hazard of death, and consequently a relatively poor predicted survival. In order to evaluate the predictive value, leave-one-out cross-validation is used. The score threshold that produced optimal separation between good and bad prognosis was used for Kaplan-Meier analysis.

Results

The inventors performed a global miRNA expression profiling of non-mutated KRAS colorectal tumor tissue samples using the Illumina Human microRNA Expression Profiling Assay v2 which measures the expression levels of 1145 miRNAs. On the 1145 analyzed miRNA, one shows a correlation between its expression level and the prognosis. FIG. 1 shows that hsa-miR-31-3p exhibits significant different expression levels in tumor samples that highly correlates with survival and displays prediction prospective for disease-free (PFS) and overall (OS) survivals. While other miRNAs were found to be significantly correlated to prognosis ($p<0.05$), the following miRNAs were not found to be significantly correlated to prognosis ($p>0.05$): hsa-miR-29a, hsa-let-7d,hsa-miR-100, hsa-miR-1260, hsa-miR-25, hsa-let-7i, hsa-miR-146a,hsa-miR-594-pre,hsa-miR-24, hsa-miR-1826, hsa-miR-30c-2*, hsa-miR-34b*, hsa-miR-34c-3p, hsa-miR-34c-5p, hsa-miR-489, hsa-miR-191, hsa-miR-491-5p, hsa-miR-130a, hsa-miR-149, hsa-miR-193a-3p, hsa-miR-27a, hsa-miR-30a*, hsa-miR-30a, hsa-miR-30c-2*, hsa-miR-30c, hsa-miR-30e*, hsa-miR-320a, hsa-miR-320b, hsa-miR-320c, hsa-miR-362-5p, hsa-miR-500*, hsa-miR-500, 502-3p, hsa-miR-532-3p, hsa-miR-532-5p, hsa-miR-652, hsa-miR-671-5p, hsa-miR-146b-3p,hsa-miR-486-5p, hsa-let-7b, hsa-let-7e, hsa-miR-17*,hsa-miR-212, hsa-miR-128b, hsa-miR-21, and hsa-miR-23b.

Figure 2:
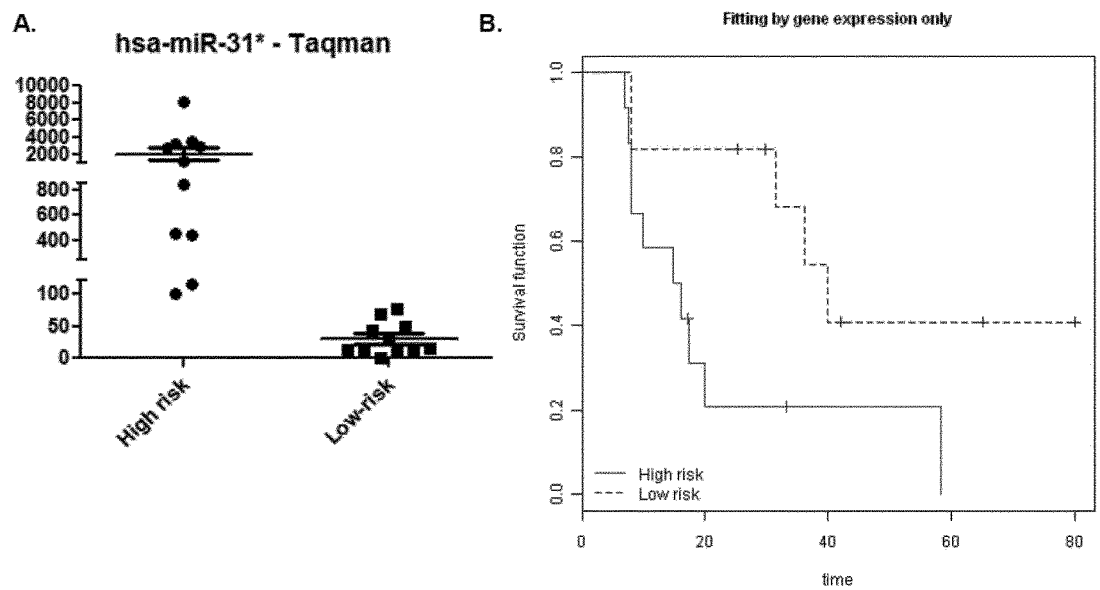
FIG. 2A is a graph that show the expression level quantified by quantitative RT-PCR (n=23; mean±SEM). Molecular weights are shown. P<0.0001.
FIG. 2B shows Kaplan-Meier model of survival for non-mutated KRAS patients with colorectal cancer, grouped by high expression (n=12) or low expression (n=11) of hsa-miR-31-3p, using the threshold of expression that optimized the predictive value. In this Cox proportional hazards model, p=0.02. The p-value is testing the hypothesis if expression data is predictive of survival. Permutation p-value of the log-rank test based on 100 permutations: p=0.08.

To further investigate the stability of the predictor risk groups, real-time miRNA quantitative PCR analysis using specific TaqMan pre-designed assays was performed on samples of 23 patients all receiving cetuximab as an EGFR inhibitor in order to quantify the expression levels of the miRNA. A fair correlation was noted between the hsa-miR-31-3p expression level measured by the two technologies with $r=0.88$. hsa-miR-31-3p exhibited significant different expression levels between tumor samples from patients with a bad prognosis and samples from patients with a good prognosis (FIG. 2). Coefficients of the fitted Cox proportional hazards model using the principal components from the training dataset were estimated to be 3.271 for PFS and 3.061 for OS. A sample was predicted to be at high/low risk if its prognostic score was larger than/smaller than or equal to −0.098088 (PFS) and −0.0918 (OS).

PPV is the probability that a sample to be predicted as responder actually belongs to the responder group. NPV is the probability that a sample predicted as non responder actually does not belong to the responder group.

A total of 9 of the 11 patients with a low level of hsa-miR-31-3p expression survived for more than 25 weeks as disease-free and displayed overall survival over 14 months (PPV=82%, [95% CI: 48%-98%]) whereas 8 of the 12 patients with a high level of hsa-miR-31-3p expression displayed disease progression within 25 weeks and died within 14 months (NPV=67% [95% CI: 35%-90%]). These values suggest a specificity for survival of 80% [95% CI: 44%-97%] for hsa-miR-31-3p expression (8/10) and a sensitivity of 69% [95% CI: 38%-91%](9/13).

The prognostic score can then be computed by the following formulae:

PFS score=$0.203738*x-1.453362$ wherein $x$ is the logged expression of hsa-miR-31-3p OS score=$0.190677*x-1.360191$ wherein $x$ is the logged expression of hsa-miR-31-3p To validate the predictive ability of the hsa-miR-31-3p, the expression level of this miRNA was measured by TaqMan in 4 independent samples (1 panitumumab treatment, 1 (cetuximab+5FU+Irinotecan) treatment, and 2 (cetuximab+Irinotecan) treatments) and the prognostic score was computed (Table 1). Two patients were predicted to be in high risk survival group and 2 in low risk survival group. One of the two patients with low hsa-miR-31-3p expression displayed overall survival over 34 months suggesting a PPV of 50%, one of the two patients with a high level of hsa-miR-31-3p died within 9 months indicating a NPV of 100% since the survival of second patient is still censored. These values suggest a specificity for survival of 50% for hsa-miR-31-3p expression (1/2) and a sensitivity of 100% (1/1).

TABLE 1

Expression level and prognostic score

| Sample | Survival time in weeks (PFS) | Censoring indicator (PFS) | Survival time in months (OS) | Censoring indicator (OS) | Predicted risk (Taqman) | hsa-miR31-3p expression (Taqman) |
|---|---|---|---|---|---|---|
| 405_T | 7.3 | 1 | 2.8 | 1 | low | 15.66 |
| 406_T | 16.3 | 1 | 5.0 | 0 | high | 2481.18 |
| 417_T | 10.7 | 1 | 34.6 | 1 | low | 31.64 |
| 421_T | 15.7 | 1 | 8.8 | 1 | high | 787.69 |

"Survival time" indicates the time from the beginning of the observation period (e.g., surgery) to a relapse event (PFS, weeks) or a death event (OS, months) of the patient.

The "Censoring indicator" marks the event of interest (relapse or death) which has occurred at the observation time. 1: individuals with event times; 0: censored observation that occurs when the individual does not have any event during the observation time, or when the observation is incomplete.

The "Predicted Risk" is specified as 'low' (low risk of death) or 'high' (high risk of death) according to the PFS score threshold.

"hsa-miR31-3p expression" represents the level of expression of hsa-miR31-3p (in arbitrary units.)

Example 2

Confirmation of the Prognostic Power of the miRNA in Patients Treated with Different Anti-EGFR and Elaboration of a Prognostic Nomogram Patients and Methods The training set (group 1) of patients is composed of 33 patients, 24 males and 9 females. The mean of age is 58.58±11.6 years. Among them, 24 received a (cetuximab+Irinotecan) treatment, 5 a (cetuximab+5FU+Irinotecan) treatment, 2 a (cetuximab+5FU+oxaliplatine) treatment, 1 a (cetuximab+xeloda) treatment, and 1 a (panitumumab+Irinotecan) treatment. 11 responded and 21 did not respond to the treatment.

The validation set is composed of 38 patients from two independent groups of 19 patients each:
- One of this group of patients (group 2), comprises 19 patients, 11 males, 8 females, with a mean age of 67.65±11.61 years. Among them, 11 received a (cetuximab+Irinotecan) treatment, 4 a (cetuximab+5FU+Irinotecan) treatment, and 4 a panitumumab treatment. 4 responded and 15 did not respond to the treatment.
- The other group of patients (group 3), comprises 19 patients, 12 males, 7 females, with a mean age of 61.84±12.28 years. All had a metastatic disease at the time of the inclusion in this study. All these patients developed a KRAS wild type colon cancer. All received a (panitumumab+Irinotecan) treatment. 8 responded and 11 did not respond to the treatment.

Determination of the KRAS status, quantification of miRNA expression levels and statistical analysis were performed as explained in Example 1.

BRAF status was determined on tumor sample, by an allelic discrimination assay (as described in Lievre et al, Cancer Res, 2006. 66: 3992-3995; and Laurent-Puig P, et al, J Clin Oncol. 2009, 27(35):5924-30). The BRAF gene in the tumor cells was considered as wild-type if the BRAF gene does not show substitution V600E (T1799A).

Survival model prediction was calculated as in Example 1.

The response status of the patients was assessed according to RECIST criteria. The median of follow-up until progression was 19.86 weeks and the median overall survival was 11.67 months.

Results

Figure 3:
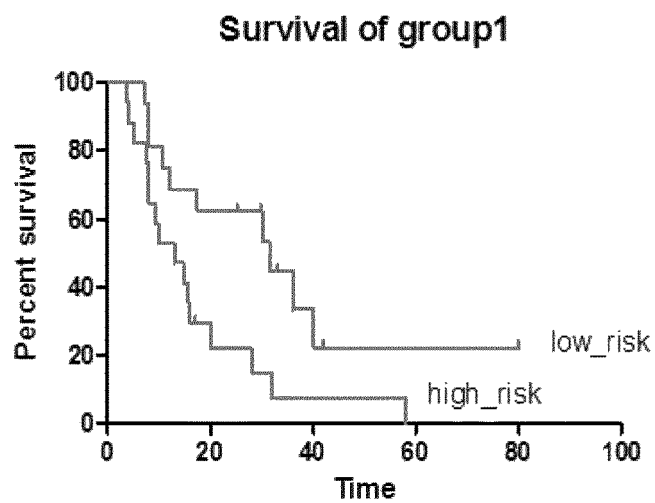
FIG. 3 shows Kaplan-Meier model of survival for non-mutated KRAS patients with colorectal cancer, grouped by high expression (n=17) or low expression (n=16) of hsa-miR-31-3p, using the threshold of expression that optimized the predictive value. In this Cox proportional hazards model, p=0.016.

Real-time miRNA quantitative PCR analysis using specific TaqMan pre-designed assays was performed to quantify the expression levels of the hsa-miR31-3p on the training set of 33 patients. hsa-miR31-3p exhibited significant different expression levels between tumor samples from patients with a bad prognosis and samples from patients with a good prognosis (FIG. 3). Coefficients of the fitted Cox proportional hazards model using the principal components from the training dataset were estimated to be 3.388 for PFS. A sample was predicted to be at high/low risk if its prognostic score was larger than/smaller than or equal to −0.03123 (PFS).

A total of 10 of the 16 patients with a low risk had a low expression level of hsa-miR31-3p expression survived for more than 25 weeks as disease-free giving a PPV=63% [95% CI: 35%-85%], whereas 13 of the 17 patients with a high level of hsa-miR31-3p expression displayed disease progression within 20 weeks giving a NPV=76%[95% CI: 50%-93%]. These values suggest a specificity of 68% % [95% CI: 43%-87%]($13/19$) for hsa-miR31-3p expression and a sensitivity of 71% [95% CI: 41%-91%] ($10/14$).

The prognostic free survival score can be computed by the following formulae:

$$\text{PFS score} = 0.178366 \cdot x - 1.363693 \text{ where } x \text{ is the logged expression of hsa-miR31-3p.}$$

Figure 4:
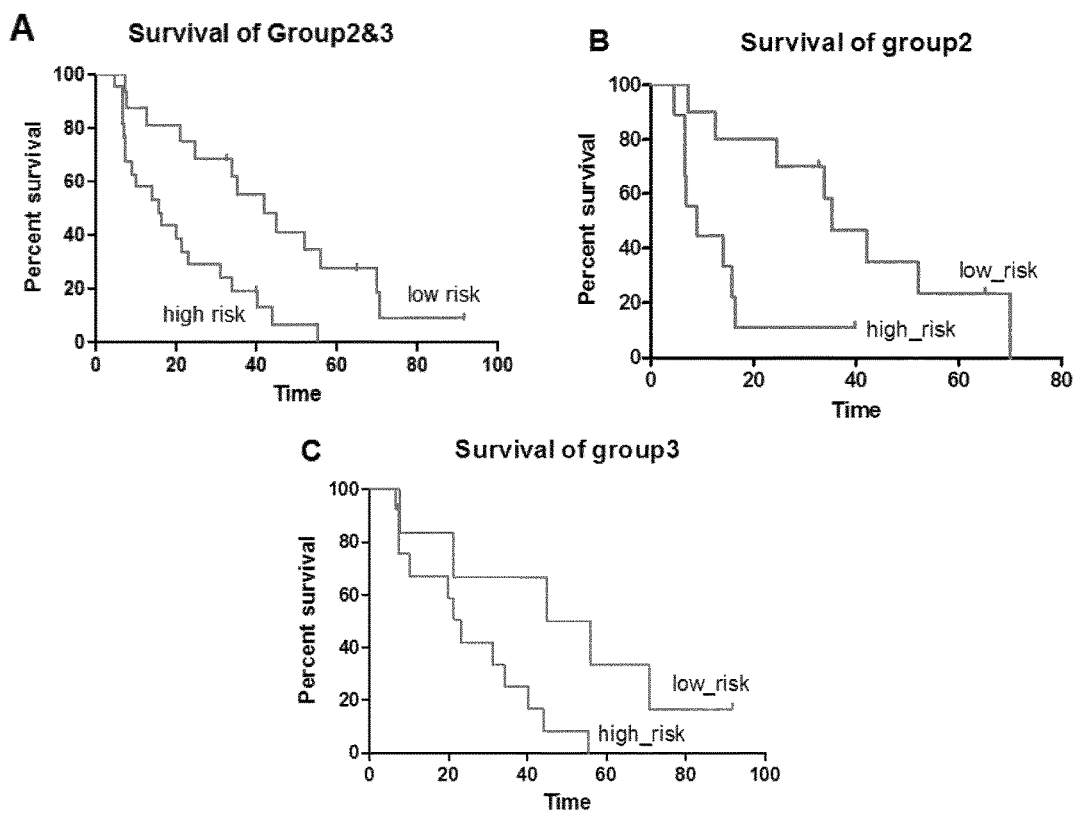
FIGS. 4A to 4C show Kaplan-Meier model of progression free survival for non-mutated KRAS patients with colorectal cancer, grouped by high expression or low expression of hsa-miR-31-3p, using the threshold of expression that optimized the predictive value.

To validate the predictive ability of the hsa-miR31-3p, the expression level of this miRNA was measured by TaqMan in 38 independent samples. We applied the multivariate model obtained from group 1 to group 2 and 3 in order to predict the disease free survival of the patients. With Mantel-Cox test and Gehan-Breslow-Wilcoxon test, the survival rate is significantly different between the sample from patients with a bad prognosis samples and patients with a good prognosis. If the validation set is split with the receiving treatment, the significant results remains in the group 2 and for the group 3 with Mantel-Cox test (FIG. 4). 13 of the 16 patients with low hsa-miR31-3p expression displayed a progression free survival (PFS) over 21 weeks giving a PPV of 81% [95% CI: 54%-96%], 14 of the 22 patients with a high level of hsa-miR31-3p displayed a PFS under 20 months giving a NPV of 64% [95% CI: 41%-83%]. These values suggest a specificity of 82% [95% CI: 56%-96%] for hsa-miR31-3p expression and a sensitivity of 62% [95% CI 38%-82%].

Figure 5:
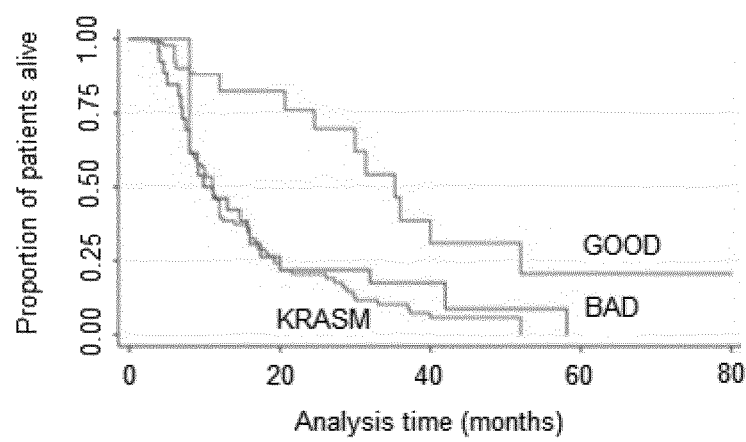
FIG. 5. Kaplan-Meier model of survival for KRAS mutated patients (KRASM), and two KRAS wild-type patients populations segregated based on hsa-miR31-3p expression level and associated prognosis (GOOD: good prognosis based on hsa-miR31-3p expression, and BAD: bad prognosis based on hsa-miR31-3p expression).

In addition, evaluation of prognosis based on hsa-miR31-3p expression level is clinically highly significant, since KRAS wild type patients with high hsa-miR31-3p expression, who were up to now considered as likely to respond based only on KRAS status, actually have very low chances of responding to anti-EGFR antibodies and thus a very bad prognosis. This is illustrated in FIG. 5, which shows survival curves of KRAS mutated patients (KRASM), and two KRAS wild-type patients populations segregated based on hsa-miR31-3p expression level and associated prognosis (good prognosis for low hsa-miR31-3p expression, and bad prognosis for high hsa-miR31-3p expression). The survival curve of the KRAS mutated patients (KRASM) is similar to the survival curve of the KRAS wild-type patients classified in bad prognosis group by the expression level of hsa-miR31-3p (BAD). This suggests the total ineffectiveness of the anti-EGFR treatment when patients are classified as "high-risk" by the expression level of hsa-miR31-3p.

Figure 6:
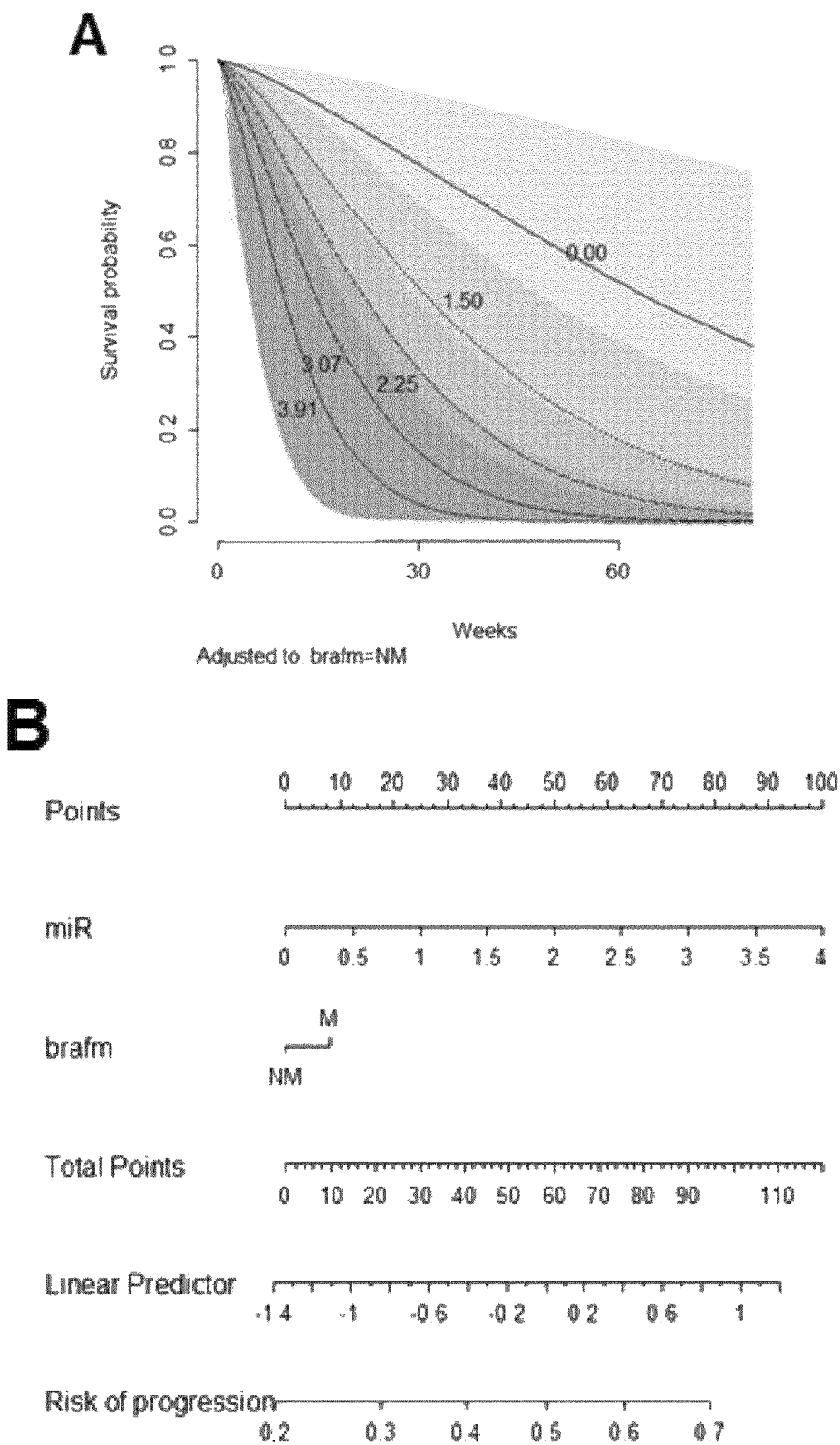
FIG. 6A: Model-building analysis performed to develop multivariate logistic regression models that used BRAF mutational status and log. miR expression factors to predict the likelihood of progression (PFS).
FIG. 6B: Nomograms for PFS to predict survival risk progression constructed based on BRAF mutational status (brafm, NM: non mutated; M: mutated) and log. miR expression (miR). To individualize risk prediction of each patient, points are allocated to each of the variable by selecting the corresponding points from the points scale, e.g. a patient with a mutated BRAF would score 8 points; a patient with log.miR=0.5 would score 12 points. A sum of the points is then plotted on the Total Points scale which corresponds to a predicted rate of progression. After 150 bootstrap runs, the concordance indices of the nomograms for PFS were 0.75.

With these results, multivariate Cox proportional hazards models with BRAF mutational status and log.miR expression as covariates were used to construct a nomogram for PFS to predict the likelihood of progression (see FIGS. 6A and 6B). We divided the available data from patients into the training set (including the patients from group1), used to develop the prediction model, and the validation set (including the patients from group 2&3). The prediction accuracy of the model was quantified on the independent validation dataset using i) the concordance index, which is numerically equivalent to the area under the receiver operating characteristic curve (0.7535888) and ii) a Univariate Cox Survival analysis done based on risk of progression score (p<0.0001). (FIG. 6B) Its shows the correlation between the expression level of the hsa-miR31-3p and the progression free survival. The more the expression level of the hsa-miR31-3p, the less the prognostic is good.

Figure 7:
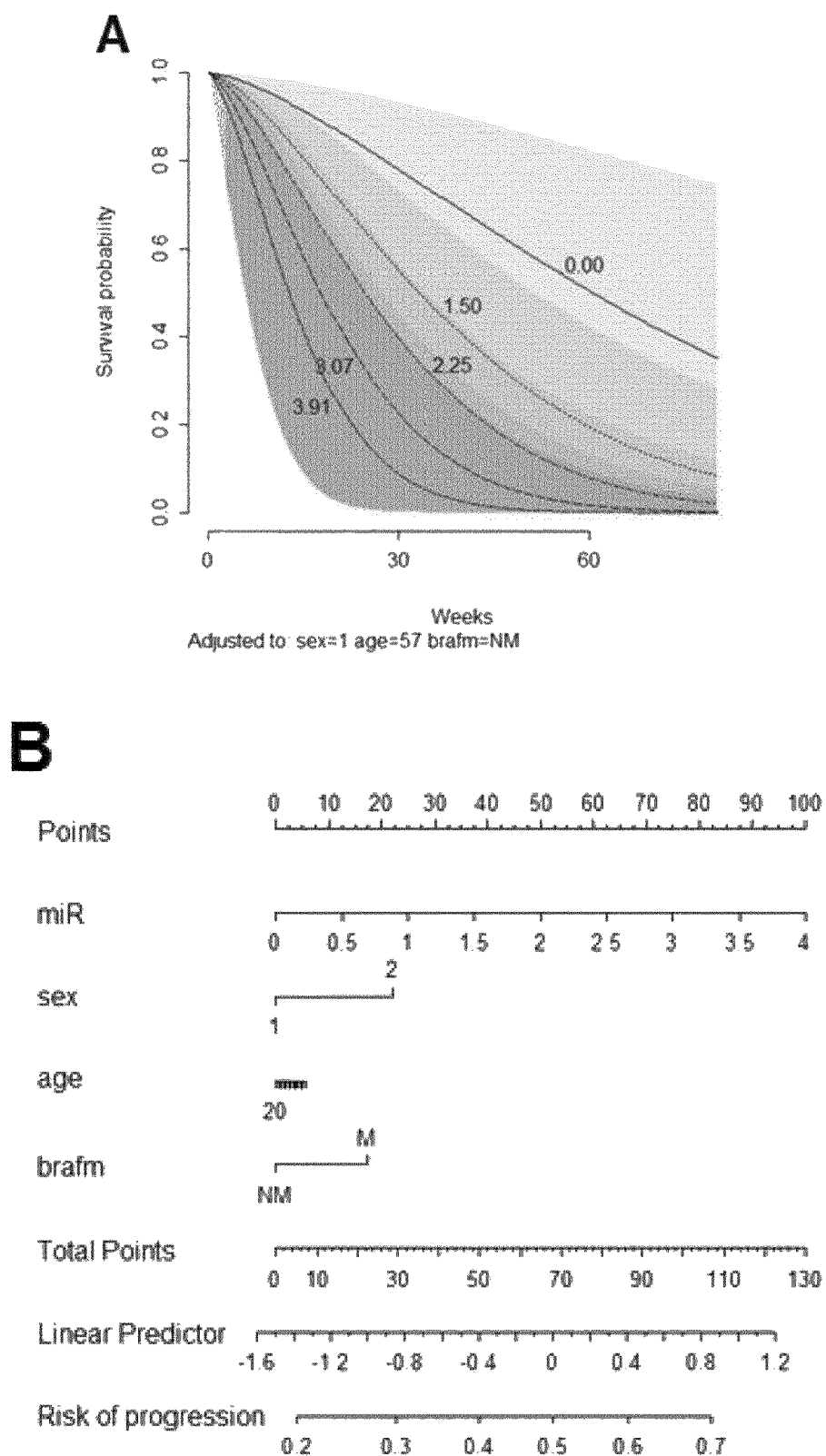
FIG. 7A: Model-building analysis performed to develop multivariate logistic regression models that used BRAF mutational status, age, gender and log. miR expression factors to predict the likelihood of progression (PFS).
FIG. 7B: Nomograms for PFS to predict survival risk progression constructed based on BRAF mutational status (brafm, NM: non mutated; M: mutated), age, gender (sex, 1: male, 2: female) and log. miR expression (miR). To individualize risk prediction of each patient, points are allocated to each of the variable by selecting the corresponding points from the points scale, e.g. a patient with mutation BRAF would score 17 points; a patient with sex=2 would score 22 points, a patient would score 1 point by 10 years over 25 years, a patient with log.miR=0.5 would score 12 points. A sum of the points is then plotted on the Total Points scale which corresponds to a predicted rate of progression. After 150 bootstrap runs, the concordance indices of the nomograms for PFS was 0.77.

Another nomogram based on the expression level of the hsa-miR31-3p was elaborated taking into account the age, the gender and the presence or absence of BRAF mutation with prediction accuracy of the model being AUC=0.77 and univariate cox p<0.0001. (FIGS. 7A and 7B)

Example 3

Correlation Between Formalin Fixed-paraffin Embedded Samples and Frozen Tumor Sample Results, and Confirmation of the Predictive Value of the Nomogram Elaborated on FFPE Independent Tumor Samples Patients and Methods The patients sample is composed of 41 patients, 27 males and 14 females. The mean of age is 60.5±12.4 years. All patients progressed on irinotecan-based chemotherapy, and then received Panitumumab at a dose of 6 mg/kg on day 1 as a 60-min intravenous infusion, just before the administration of irinotecan 180 mg/m² in 90 min on day 1 of each fortnightly cycle (cycles are every 14 days). For all of these patients formalin fixed-paraffin embedded (FFPE) tumors samples were available, and for 15 of them, frozen tumors samples were available as well, allowing a direct comparison of the hsa-miRNA-31-3p levels of expression between the two samples types.

Small RNA were extracted from FFPE tumors samples using the miRNeasy extraction kit (Qiagen) and from frozen tumors sample using mirVanamiRNA Isolation Kit from Ambion.

Regression analysis has been performed to compare the frozen and the FFPE values on the same patients (n=15). A linear regression model attempts to explain the relationship between both variables was done using a straight line that allowed the determination of an equation that fit the data.

Determination of the KRAS and BRAF status, quantification of miRNA expression levels and statistical analysis were performed as described in Example 1 and 2. Two patients were excluded because of the presence of KRAS mutations. The response status of the patients was assessed according to RECIST criteria. Among the 39 patients, 17 responded, 21 did not respond to the treatment and a patient was nor evaluable. The median of follow-up until progression was 28.3 weeks and the median overall survival was 12.9 months.

Survival analysis and model prediction were performed on the remaining 39 patients as described in Example 2.

Results

Real-time miRNA (miR) quantitative PCR analysis using specific TaqMan pre-designed assays was performed on the FFPE and frozen samples to quantify the expression levels of the hsa-miR31-3p on all 39 patients.

Figure 8:
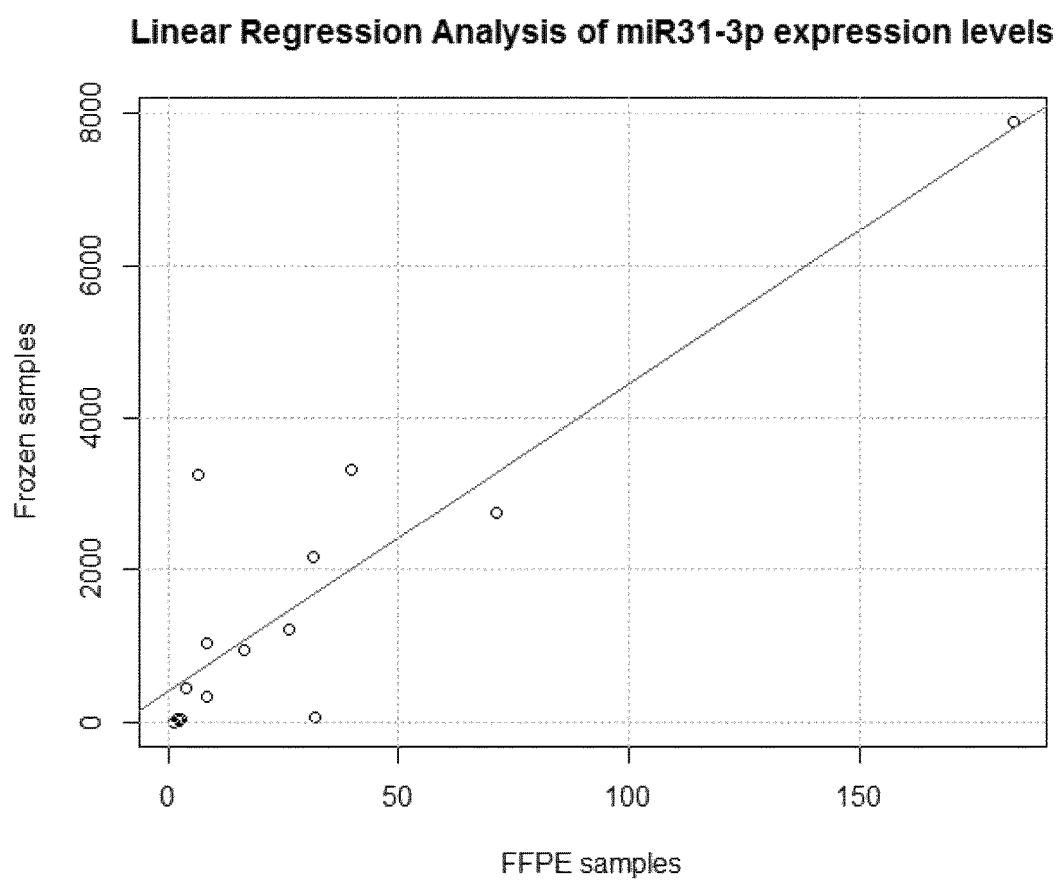
FIG. 8. Scatter plot of the expression levels of miR31-3p in the FFPE samples versus frozen samples. A linear regression analysis shows a close relationship between both variables that may be represented by a straight line and computed mathematically as y=40.439*x−397.3. The circle indicate individual samples; line, linear regression.

A linear regression model (see FIG. 8) produced a strong correlation (adjusted $R^2=0.78$) between the expression values of 13 frozen and corresponding FFPE samples and estimated no real evidences against linearity (p=7.6e-06, F-test=50.98, DF=13), yielding the following equation:

$y=40.439*x-397.3$, wherein y corresponds to the expression level of hsa-miR-31-3p in the frozen patient's samples and x corresponds to the expression level of hsa-miR-31-3p in the corresponding FFPE patient's samples. The formula was used to determine a 'frozen-expected' (FE) expression value on each collected FFPE sample.

Figure 9:
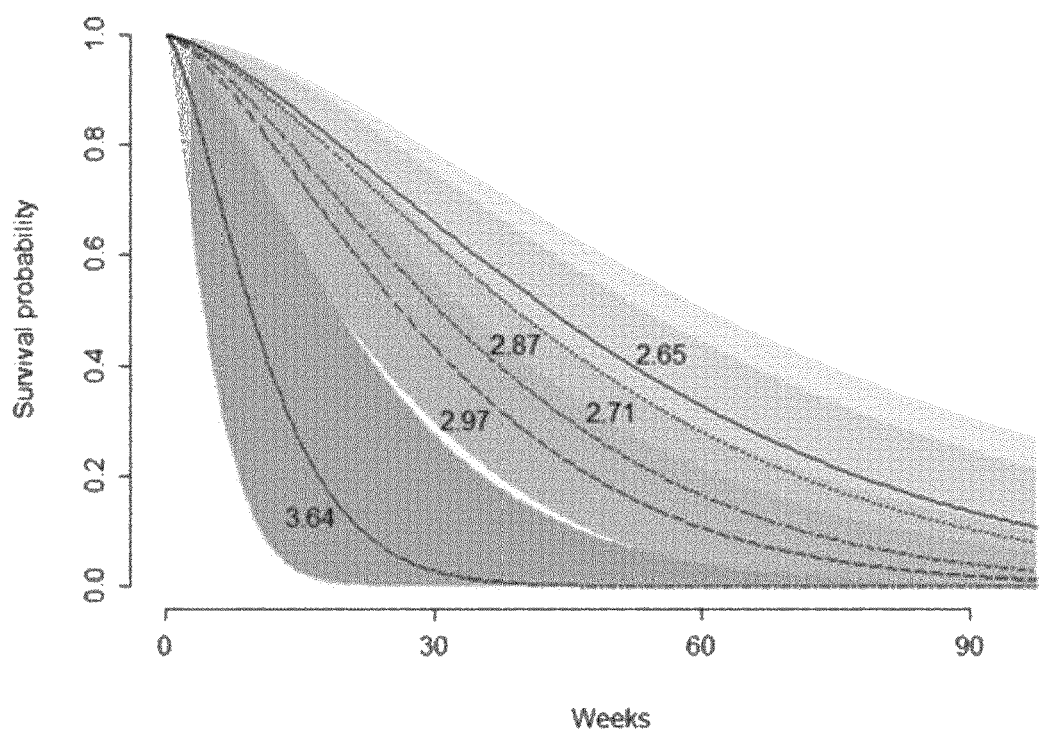
FIG. 9. Logistic regression model to predict the likelihood of progression (PFS) performed on the 'frozen-expected' (FE) levels of expression of the hsa-miR-31-3p. The curves correspond to the quartile distribution of the expression levels (in log base 10) of miR. The grey color shapes the 95% confidence interval.

Univariate survival analysis with the Cox proportional hazard model confirmed the predictive value on survival risk progression of the FE levels of expression of the hsa-miR-31-3p (Wald test, p=0.004) alone (see FIG. 9).

Figure 10:
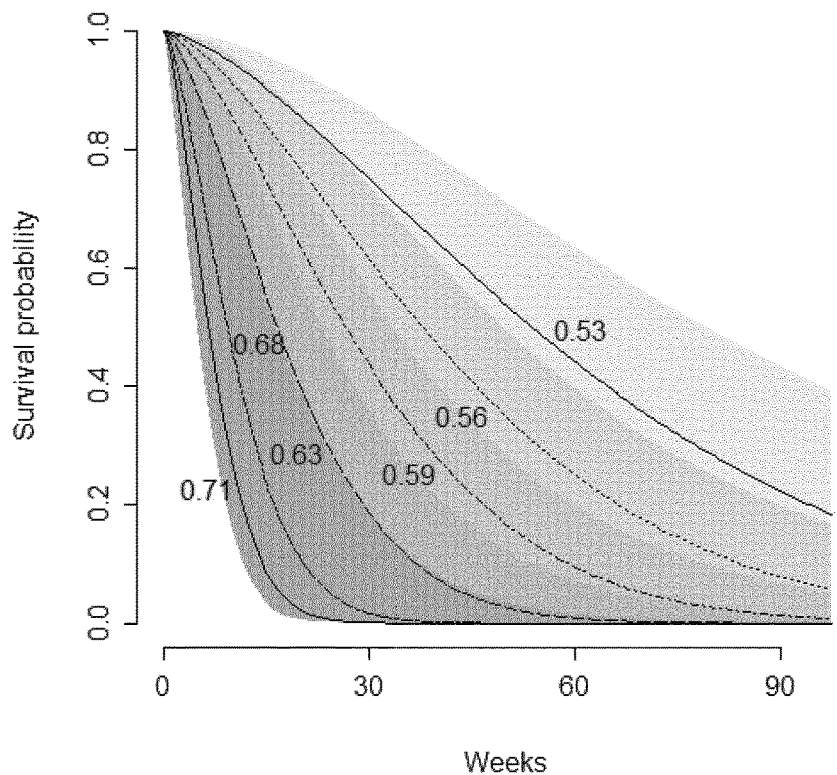
FIG. 10. Logistic regression model to predict the likelihood of progression (PFS) performed on the 'risk of progression' score computed from the PFS based nomogram elaborated in Example 2 using both the BRAF mutational status and the log expression of hsa-miR31-3p. The figures on the curves correspond to scores. The grey color shapes the 95% confidence interval.

The prediction accuracy of the FE levels of expression of the hsa-miR-31-3p was also measured based on the nomogram for PFS elaborated in Example 2 using both BRAF mutational status and log.miR expression. After 150 bootstrap runs, the model displayed a concordance index of 0.664. Each sample value resulted in a 'risk of progression' score (as described in Example 2) that is found to be predictive of the survival risk of progression (Wald test, p=0.0005) (see FIG. 10).

BIBLIOGRAPHIC REFERENCES

Albitar L et al. Mol Cancer 2010; 9:166;
Ambros V et al, RNA 2003 9(3):277-279;
Bair E. & R Tibshirani, PLOS Biology 2:511-522, 2004;
Bos. Cancer Res 1989; 49:4682-4689;
Bustin et al., 2005, Clin. Sci., 109:365-379;
Chan S L et al. Expert Opin Ther Targets. 2012 March; 16Suppl 1:S63-8;
Chang K W et al. Oral Oncol. 2012 Jul. 30,
Chu H et al. Mutagenesis. 2012 Oct. 15;
Ciardello F et al. N Engl J Med. 2008 Mar. 13; 358(11): 1160-74;
Cox, D. R. (1972). Journal of the Royal Statistical Society, Series B 34 (2), 187-220;
Cunningham et al, N Engl Med 2004; 351: 337-45;
Demiralay et al. Surgical Science, 2012, 3, 111-115;
Edkins et al. Cancer Biol Ther. 2006 August; 5(8): 928-932
Eisenhauer et al, European Journal of Cancer, 2009, 45:228-247;
Griffiths-Jones S. NAR 2004 32(Database Issue):D109-D111;
Griffiths-Jones S et al. NAR 2006 34(Database Issue):D140-D144;
Griffiths-Jones S et al. NAR 2008 36(Database Issue):D154-D158;
Hatakeyama H. et al. PLoS One. 2010 Sep. 13; 5(9):e12702;
Kozomara A et al. NAR 2011 39(Database Issue):D152-D157;
Laurent-Puig P, et al, J Clin Oncol. 2009, 27(35):5924-30;
Leboulleux S et al. Lancet Oncol. 2012 September; 13(9): 897-905;
Leslie K K et al. Gynecol Oncol. 2012 November; 127(2): 345-50;
Li Y et al. Oncol Rep. 2010 October; 24(4):1019-28;
Liebner D A et al. Ther Adv Endocrinol Metab. 2011 October; 2(5):173-95;
Lievre et al, Cancer Res. 2006 66(8):3992-5;
Lievre et al. J Clin Oncol. 2008 Jan. 20; 26(3):374-9;
Mimeault M et al. PLoS One. 2012; 7(2):e31919;
Mosakhani N. et al. Cancer Genet. 2012 Oct. 22.doi:pii: S2210-7762(12)00229-3. 10.1016/j.cancergen.2012.08.003;
Ogino S, et al. J Mol Diagn 2008; 7:413-21;
Pan J et al. Head Neck. 2012 Sep. 13;
Ragusa M. et al. Mol Cancer Ther. 2010 December; 9(12): 3396-409;
Shepherd F A, et al, N Engl J Med 2005; 353:123-132;
Tam et al. Clin Cancer Res 2006; 12:1647-1653;
Thomasson M et al. Br J Cancer 2003, 89:1285-1289;
Thomasson M et al. 2012 May 3; 5:216;
U.S. Pat. No. 7,101,663;
Wheeler D L et al. Nat Rev Clin Oncol. 2010 September; 7(9): 493-507;
WO2009/080437;
WO2010/121238;
WO2011/135459;
Xiao W et al. 2012. PLoS ONE 7(6): e38648;
Zeineldin R et al. J Oncol. 2010; 2010:414676,
Zhao L. et al. Int J Biochem Cell Biol. 2012 November; 44(11):2051-9.

The invention claimed is:

1. A method for treating a patient affected with a cancer, which method comprises:
   (i) taking a biological sample from the patient affected with a cancer,
   (ii) measuring in vitro the expression level of hsa-miR-31-3p (SEQ ID NO:1) miRNA in the biological sample of said patient,
   (iii) determining whether the patient is likely to respond to an EGFR inhibitor based on the measured expression level of hsa-miR-31-3p from step (ii), and
   (iv) administering an EGFR inhibitor to said patient if the patient has been determined to be likely to respond to the EGFR inhibitor;
   wherein the patient is affected with a cancer selected from the group consisting of colorectal, breast, lung, ovarian, endometrial, thyroid, nasopharynx, prostate, head and neck, liver, kidney, pancreas, bladder, and brain cancer.

2. The method according to claim 1, further comprising, if the patient has been determined to be unlikely to respond to the EGFR inhibitor, a step (v) of administering an alternative anticancer treatment to the patient.

3. The method according to claim 1, wherein the patient is affected with a colorectal cancer.

4. The method according to claim 2, wherein the patient is affected with a colorectal cancer, and the alternative anticancer treatment administered to the patient is selected from:
   a. a VEGF inhibitor, advantageously in combination with FOLFOX or FOLFIRI chemotherapy, or
   b. 5-FU, optionally in combination with Mitomycin B.

5. The method according to claim 1, wherein the patient is affected with a breast cancer or a lung cancer.

6. The method according to claim 1, wherein the EGFR inhibitor is an anti-EGFR antibody.

7. The method according to claim 1, wherein the EGFR inhibitor is a tyrosine kinase EGFR inhibitor.

8. The method of claim 1, wherein the patient has a KRAS wild-type cancer.

9. The method of claim 1, wherein the biological sample is a tumor tissue biopsy or whole or part of a tumor surgical resection.

10. The method of claim 1, wherein the level of expression of the miRNA is determined by quantitative RT-PCR.

11. The method of claim 1, wherein the lower the level of expression of the miRNA is, the more likely the patient is to respond to the EGFR inhibitor treatment.

12. The method of claim 1, further comprising determining a prognostic score based on the expression level of the miRNA, wherein the prognostic score indicates whether the patient is likely to respond to the EGFR inhibitor.

13. The method of claim 12, wherein the prognostic score is of formula:

Prognosis score=$a*x+b$, wherein:
- x is the logged expression level of hsa-miR-31-3p measured in the patient's sample,
- a and b are parameters that have been previously determined based on a pool of reference samples, and
- the patient is predicted as responding to the EGFR inhibitor if his/her prognosis score is lower than or equal to a threshold value c, and not responding to the EGFR inhibitor if its prognosis score is greater than threshold value c, wherein the value of c has been determined based on the same pool of reference samples.

14. The method of claim 13, wherein a, b and c are in the following ranges:

a: (0.1; 0.25);
b: (−2; −0.5);and
c: (−0.11; −0.01).

15. The method of claim 1, further comprising determining the BRAF status of said patient, and calculating a composite score taking into account the expression level of hsa-miR-31-3p and the BRAF status, wherein the composite score indicates whether the patient is likely to respond to the EGFR inhibitor.

16. The method of claim 1, wherein:
a) the cancer is colorectal cancer and the EGFR inhibitor is an anti-EGFR antibody; or
b) the cancer is lung cancer and the EGFR inhibitor is a tyrosine kinase EGFR inhibitor.

17. The method of claim 1, wherein:
a) the cancer is colorectal cancer and the EGFR inhibitor is an anti-EGFR antibody, wherein the anti-EGFR antibody is cetuximab or panitumumab; or
b) the cancer is lung cancer, which is non small cell lung cancer (NSCLC) and the EGFR inhibitor is a tyrosine kinase EGFR inhibitor, wherein the tyrosine kinase EGFR inhibitor is Erlotinib, Gefitinib, or Lapatinib.

* * * * *